United States Patent
Yamanaka et al.

(10) Patent No.: US 9,447,408 B2
(45) Date of Patent: Sep. 20, 2016

(54) METHOD OF EFFICIENTLY ESTABLISHING INDUCED PLURIPOTENT STEM CELLS

(75) Inventors: Shinya Yamanaka, Kyoto (JP); Yoshinori Yoshida, Kyoto (JP); Hidaka Yokota, Kyoto (JP)

(73) Assignee: Kyoto University, Kyoto (JP)

( * ) Notice: Subject to any disclaimer, the term of this patent is extended or adjusted under 35 U.S.C. 154(b) by 0 days.

(21) Appl. No.: 13/822,906

(22) PCT Filed: Sep. 14, 2011

(86) PCT No.: PCT/JP2011/071539
§ 371 (c)(1),
(2), (4) Date: Mar. 13, 2013

(87) PCT Pub. No.: WO2012/036299
PCT Pub. Date: Mar. 22, 2012

(65) Prior Publication Data
US 2013/0183759 A1    Jul. 18, 2013

Related U.S. Application Data

(60) Provisional application No. 61/382,707, filed on Sep. 14, 2010.

(51) Int. Cl.
*C12N 15/00* (2006.01)
*C12N 5/074* (2010.01)
*C12N 15/01* (2006.01)

(52) U.S. Cl.
CPC ............. *C12N 15/00* (2013.01); *C12N 5/0696* (2013.01); *C12N 15/01* (2013.01); *C12N 2501/998* (2013.01)

(58) Field of Classification Search
CPC ................. C12N 5/0696; C12N 15/01; C12N 2501/998
See application file for complete search history.

(56) References Cited

U.S. PATENT DOCUMENTS

2012/0028351 A1 * 2/2012 Li et al. .................... 435/350
2012/0100568 A1   4/2012 Pei et al.

FOREIGN PATENT DOCUMENTS

| CN | 101580816 A | 11/2009 |
|---|---|---|
| WO | WO 2009/117439 A2 | 9/2009 |
| WO | WO 2009/157593 A1 | 12/2009 |
| WO | WO 2010/077955 A1 | 7/2010 |

OTHER PUBLICATIONS

European Patent Office, Extended European Search Report in European Patent Application No. 11825297.2 (Jan. 20, 2014).
Hong et al., *Nature*, 460(7259): 1132-1135 (2009).
Huangfu et al. *Nature Biotechnology*, 26(7): 795-797 (2008).
Lin et al., *Nat. Methods*, 6(11): 805-808 (2009).
Shi et al., *Cell Stem Cell*, 2(6): 525-528 (2008).
Silva et al., *PLoS Biology*, 6(10): e253 (2008).
Zhao et al., *Cell Stem Cell*, 3(5): 475-479 (2008).
Japanese Patent Office, International Search Report in International Patent Application No. PCT/JP2011/071539 (Dec. 27, 2011).
Takahashi et al., *Nature Communications*, 5: 3678 [doi: 10.1038/ncomms4678] (Apr. 24, 2014).

* cited by examiner

*Primary Examiner* — Marcia S Noble
(74) *Attorney, Agent, or Firm* — Leydig, Voit & Mayer, Ltd.

(57) ABSTRACT

The present invention provides a method of improving the efficiency of establishment of induced pluripotent stem (iPS) cells by inhibiting p38 function in the step of somatic cell nuclear reprogramming. The 38 function can be inhibited by bringing an inhibitor selected from the group consisting of (1) a chemical inhibitor of p38 (2) a dominant negative mutant of p38 or a nucleic acid that encodes the same, (3) a nucleic acid selected from the group consisting of siRNAs and shRNAs targeted to p38 and DNAs that encode the same and (4) an inhibitor of p38 pathway into contact with a somatic cell and the like. The present invention also provides an agent for improving the efficiency of establishment of induced pluripotent stem cells, which contains an inhibitor of p38 function, particularly an inhibitor selected from the group consisting of (1) a chemical inhibitor of p38 (2) a dominant negative mutant of p38 or a nucleic acid that encodes the same, (3) a nucleic acid selected from the group consisting of siRNAs and shRNAs targeted to p38 and DNAs that encode the same and (4) an inhibitor of p38 pathway. Moreover, the present invention provides a production method of iPS cells, which includes bringing a nuclear reprogramming substance and an inhibitor of p38 function into contact with a somatic cell.

18 Claims, 5 Drawing Sheets
(5 of 5 Drawing Sheet(s) Filed in Color)

2.0 × 10⁵ Tig109 Day32 colony count 2.0 × 10⁵ Tig109 Day40 colony count

METHOD OF EFFICIENTLY ESTABLISHING INDUCED PLURIPOTENT STEM CELLS

CROSS-REFERENCE TO RELATED APPLICATIONS

This patent application is the U.S. national phase of International Patent Application No. PCT/JP2011/071539, filed on Sep. 14, 2011, which claims the benefit of U.S. Provisional Patent Application No. 61/382,707, filed Sep. 14, 2010, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 17,354 bytes ASCII (Text) file named "712413SequenceListing.txt," created Mar. 5, 2013.

TECHNICAL FIELD OF THE INVENTION

The present invention relates to a method of improving the efficiency of establishment of induced pluripotent stem (hereinafter sometimes referred to as iPS) cells and a drug therefor. More specifically, the present invention relates to a method of improving the efficiency of establishment of iPS cells by inhibiting the p38 function in the step of somatic cell nuclear reprogramming, and an agent for improving the efficiency of establishment of iPS cells with an inhibitor of p38 function as an active ingredient.

BACKGROUND OF THE INVENTION

In recent years, mouse and human iPS cells have been established one after another. Takahashi and Yamanaka (1) induced iPS cells by introducing the Oct3/4, Sox2, Klf4 and c-Myc genes into fibroblasts derived from a reporter mouse wherein the neomycin resistance gene is knocked-in into the Fbx15 locus, and forcing the cells to express the genes. Okita et al. (2) succeeded in establishing iPS cells (Nanog iPS cells) that show almost the same gene expression and epigenetic modification as those in embryonic stem (ES) cells by producing a transgenic mouse wherein the green fluorescent protein (GFP) and puromycin-resistance genes are integrated into the locus of Nanog, whose expression is more localized in pluripotent cells than Fbx15 expression, forcing the fibroblasts derived from the mouse to express the above-mentioned 4 genes, and selecting puromycin-resistant and GFP-positive cells. Similar results were confirmed by other groups (3, 4). Thereafter, it was revealed that iPS cells could also be produced with 3 factors other than the c-Myc gene (5).

Furthermore, Takahashi et al. (6) succeeded in establishing iPS cells by introducing the same 4 genes as those used in the mouse into human skin fibroblasts. On the other hand, a group of Yu et al. (7) produced human iPS cells using Nanog and Lin28 in place of Klf4 and c-Myc. Park et al. (8) produced human iPS cells using the TERT and the SV40 large T antigen, which are known as the human cell immortalizing genes, in addition to the 4 factors Oct3/4, Sox2, Klf4 and c-Myc. Hence, it has been demonstrated that iPS cells comparable to ES cells in pluripotency can be produced in both humans and mice by introducing defined factors into somatic cells.

However, the efficiency of iPS cell establishment is low at less than 1%. Especially, a problem of extremely low efficiency of iPS cell establishment occurs when they are produced by introducing 3 factors (Oct3/4, Sox2 and Klf4) is other than c-Myc, which is feared to cause tumorigenesis in tissues or individuals differentiated from iPS cells, into somatic cells.

p38 belongs to the MAP kinase (Mitogen-activated protein kinase) family and the p38 signal transduction pathway is known to be involved in environmental stress, UV light, apoptosis and inflammatory responses. In recent years, moreover, activation of p38 in cancer has also been reported (9). However, its relationship with nucleus reprogramming is not known well.

CITED DOCUMENTS

1. Takahashi, K. and Yamanaka, S., *Cell*, 126: 663-676 (2006)
2. Okita, K. et al., *Nature*, 448: 313-317 (2007)
3. Wernig, M. et al., *Nature*, 448: 318-324 (2007)
4. Maherali, N. et al., *Cell Stem Cell*, 1: 55-70 (2007)
5. Nakagawa, M. et al., *Nat. Biotethnol.*, 26: 101-106 (2008)
6. Takahashi, K. et al., *Cell*, 131: 861-872 (2007)
7. Yu, J. et al., *Science*, 318: 1917-1920 (2007)
8. Park, I. H. et al., *Nature*, 451: 141-146 (2008)
9. Junttila M R et al., *FASEB J.*, 22: 954-65 (2008)

SUMMARY OF THE INVENTION

It is an object of the present invention to provide a means of improving the efficiency of establishment of iPS cells; another object of the present invention is to provide a method of efficiently producing iPS cells using the means.

The present inventors conducted extensive investigations with the aim of accomplishing the above-described objects, and clarified that by inhibiting the p38 function in the step of somatic cell nuclear reprogramming, the efficiency of establishment of iPS cells can be remarkably increased. They have clarified that the effect is remarkable in human cells as well, and completed the present invention.

Accordingly, the present invention provides:

[1] A method of improving the efficiency of establishment of induced pluripotent stem cells, comprising a step of inhibiting p38 function during somatic cell nuclear reprogramming.

[2] The method according to [1] above, wherein the p38 function is inhibited by bringing a chemical inhibitor of p38 into contact with a somatic cell.

[3] The method according to [2] above, wherein the inhibitor is at least one substance selected from the group consisting of SB202190, SB239063 and SB203580.

[4] The method according to [1] above, wherein the p38 function is inhibited by bringing a dominant negative mutant of p38 or a nucleic acid that encodes the same into contact with a somatic cell.

[5] The method according to [1] above, wherein the p38 function is inhibited by bringing a nucleic acid selected from the group consisting of p38 siRNAs, p38 shRNAs and DNAs that encode the same into contact with a somatic cell.

[6] The method according to [1] above, wherein the p38 function is inhibited by bringing an inhibitor of p38 pathway into contact with a somatic cell.

[7] An agent for improving the efficiency of establishment of induced pluripotent stem cells, comprising an inhibitor of p38 function.

[8] The agent according to [7] above, wherein the inhibitor is a chemical inhibitor of p38.
[9] The agent according to [8] above, wherein the inhibitor is at least one substance selected from the group consisting of SB202190, SB239063 and SB203580.
[10] The agent according to [7] above, wherein the inhibitor is a dominant negative mutant of p38 or a nucleic acid that encodes the same.
[11] The agent according to [7] above, wherein the inhibitor is a nucleic acid selected from the group consisting of p38 siRNAs, p38 shRNAs and DNAs that encode the same.
[12] The agent according to [7] above, wherein the inhibitor is an inhibitor of p38 pathway.
[13] A method of producing induced pluripotent stem cells, comprising a step of bringing nuclear reprogramming substance(s) and an inhibitor of p38 function into contact with a somatic cell.
[14] The method according to [13] above, wherein the inhibitor is a chemical inhibitor.
[15] The method according to [14] above, wherein the inhibitor is at least one substance selected from the group consisting of SB202190, SB239063 and SB203580.
[16] The method according to [13] above, wherein the inhibitor is a dominant negative mutant of p38 or a nucleic acid that encodes the same.
[17] The method according to [13] above, wherein the inhibitor is a nucleic acid selected from the group consisting of p38 siRNAs, p38 shRNAs and DNAs that encode the same.
[18] The method according to [13] above, wherein the inhibitor is an inhibitor of p38 pathway.
[19] The method according to [13] above, wherein the nuclear reprogramming substances are Oct3/4, Klf4 and Sox2, or nucleic acids that encode the same.
[20] The method according to [13] above, wherein the nuclear reprogramming substances are Oct3/4, Klf4, Sox2 and at least one selected from the group consisting of c-Myc or L-Myc, Nanog, Lin28 or Lin28B, and Glis1, or nucleic acids that encode the same.
[21] An inducer of induced pluripotent stem cells, comprising nuclear reprogramming substance(s) and an inhibitor of p38 function.
[22] The inducer according to [21] above, wherein the inhibitor is a chemical inhibitor.
[23] The inducer according to [22] above, wherein the inhibitor is at least one substance selected from the group consisting of SB202190, SB239063 and SB203580.
[24] The inducer according to [21] above, wherein the inhibitor is a dominant negative mutant of p38 or a nucleic acid that encodes the same.
[25] The inducer according to [21] above, wherein the inhibitor is a nucleic acid selected from the group consisting of p38 siRNAs, p38 shRNAs and DNAs that encode the same.
[26] The inducer according to [21] above, wherein the inhibitor is an inhibitor of p38 pathway.
[27] The inducer according to [21] above, wherein the nuclear reprogramming substances are Oct3/4, Klf4 and Sox2, or nucleic acids that encode the same.
[28] The inducer according to [21] above, wherein the nuclear reprogramming substances are Oct3/4, Klf4, Sox2 and at least one selected from the group consisting of c-Myc or L-Myc, Nanog, Lin28 or Lin28B, and Glis1, or nucleic acids that encode the same.

Because inhibitors of p38 function make it possible to remarkably increase the efficiency of establishment of iPS cells, the same are particularly useful in the induction of iPS cells by means of 3 factors except c-Myc, for which the efficiency of establishment has conventionally been very low. Because c-Myc is feared to cause tumorigenesis when reactivated, the improvement in the efficiency of establishment of iPS cells using the 3 factors is of paramount utility in applying iPS cells to regenerative medicine.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
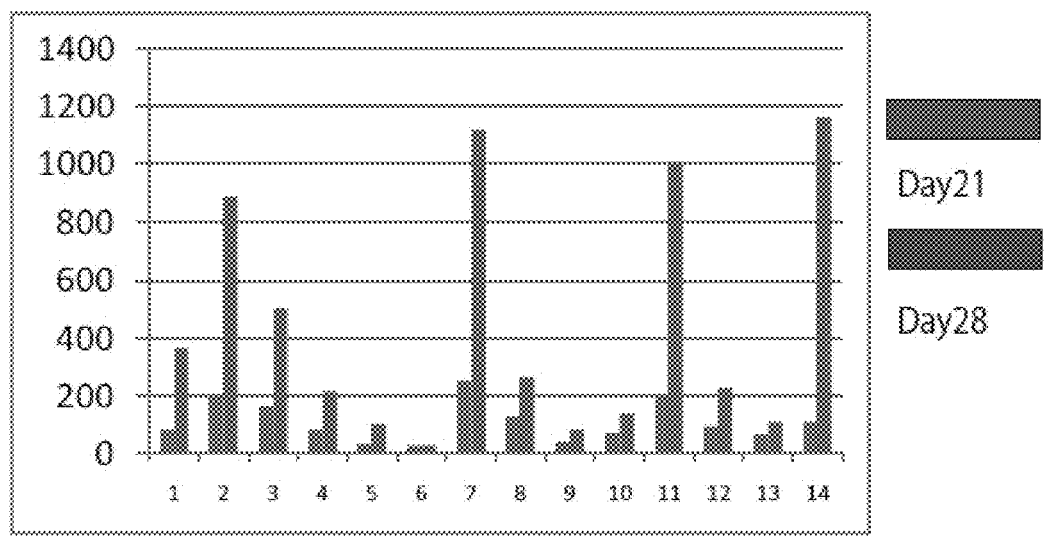
FIG. 1 is a graphic representation showing the colony counts obtained on day 21 (left bar) or 28 (right bar) after infection by introducing four genes (Oct3/4, Klf4, Sox2, C-myc) into mouse dermal fibroblasts (MEFs), and culturing the cells in the presence of various p38 inhibitors. The upper panel shows total colony counts; the lower panel shows Nanog GFP-positive colony counts. The vertical axis indicates the number of iPS cell colonies found on a 10 cm dish.
Figure 1:
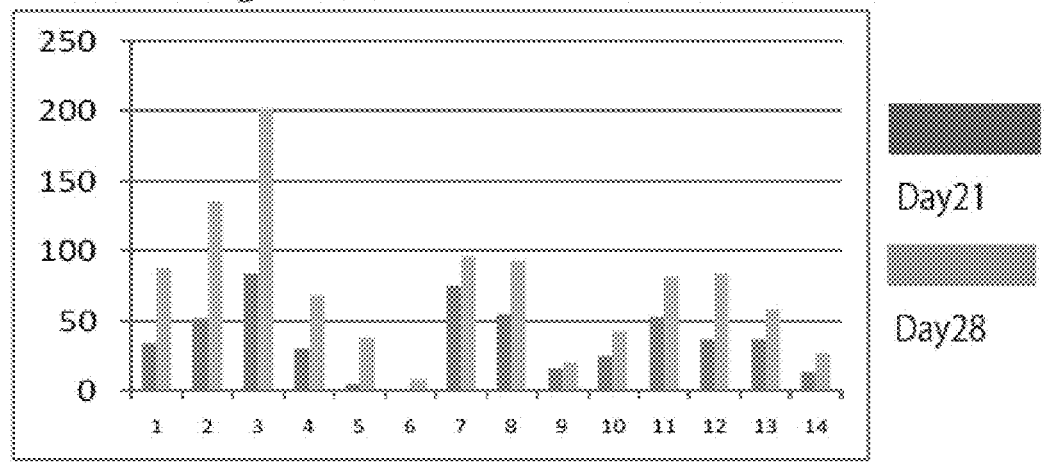

The present invention provides a method of improving the efficiency of establishment of iPS cells by inhibiting the p38 function in the step of somatic cell nuclear reprogramming.

The choice of means of inhibiting the p38 function is not particularly limited; preferably, a method wherein an inhibitor of p38 function is brought into contact with a somatic cell can be mentioned.

(a) Sources of Somatic Cells

Any cells other than germ cells of mammalian origin (e.g., humans, mice, monkeys, bovines, pigs, rats, dogs etc.) in the present invention can be used as starting material for the production of iPS cells. Examples include keratinizing epithelial cells (e.g., keratinized epidermal cells), mucosal epithelial cells (e.g., epithelial cells of the superficial layer of tongue), exocrine gland epithelial cells (e.g., mammary gland cells), hormone-secreting cells (e.g., adrenomedullary cells), cells for metabolism or storage (e.g., liver cells), luminal epithelial cells constituting interfaces (e.g., type I alveolar cells), luminal epithelial cells of the obturator canal (e.g., vascular endothelial cells), cells having cilia with transporting capability (e.g., airway epithelial cells), cells for extracellular matrix secretion (e.g., fibroblasts), constrictive cells (e.g., smooth muscle cells), cells of the blood and the immune system (e.g., T lymphocytes), sense-related cells (e.g., rod cells), autonomic nervous system neurons (e.g., cholinergic neurons), sustentacular cells of sensory organs and peripheral neurons (e.g., satellite cells), nerve cells and glia cells of the central nervous system (e.g., astroglia cells), pigment cells (e.g., retinal pigment epithelial cells), progenitor cells (tissue progenitor cells) thereof and the like. There is no limitation on the degree of cell differentiation, the age of an animal from which cells are collected and the like; even undifferentiated progenitor cells (including somatic stem cells) and finally differentiated mature cells can be used alike as sources of somatic cells in the present invention. Examples of undifferentiated progenitor cells include tissue stem cells (somatic stem cells) such as nerve stem cells, hematopoietic stem cells, mesenchymal stem cells and dental pulp stem cells.

The choice of mammal individual as a source of somatic cells is not particularly limited; however, when the iPS cells obtained are to be used for regenerative medicine in humans, it is particularly preferable, from the viewpoint of prevention of graft rejection, to collect the somatic cells from a patient or another person with the same or substantially the same HLA type as that of the patient. "Substantially the same HLA type" as used herein means that the HLA type of donor matches with that of patient to the extent that the transplanted cells, which have been obtained by inducing differentiation of iPS cells derived from the donor's somatic cells, can be engrafted when they are transplanted to the patient with use of immunosuppressant and the like. For example, it includes an HLA type wherein major HLAs (e.g., the three major loci of HLA-A, HLA-B and HLA-DR) are identical (hereinafter the same meaning shall apply) and the like. When the iPS cells obtained are not to be administered (transplanted) to a human, but used as, for example, a source of cells for screening for evaluating a patient's drug susceptibility or adverse reactions, it is likewise desired to collect the somatic cells from the patient or another person with the same genetic polymorphism correlating with the drug susceptibility or adverse reactions.

Somatic cells isolated from a mammal can be pre-cultured using a medium known per se suitable for their cultivation according to the choice of cells before being subjected to the step of nuclear reprogramming. Examples of such media include, but are not limited to, minimal essential medium (MEM), Dulbecco's modified Eagle medium (DMEM), RPMI1640 medium, 199 medium, F12 medium, and the like supplemented with about 5 to 20% fetal calf serum. When a transfer reagent such as cationic liposome, for example, is used in bringing the somatic cell into contact with nuclear reprogramming substances and an inhibitor of p38 function (and another iPS cell establishment efficiency improver mentioned below if required), it is sometimes preferable that the medium has been replaced with a serum-free medium so as to prevent the transfer efficiency from decreasing.

(b) Inhibitors of p38 Function

As mentioned herein, "an inhibitor of p38 function" may be any substance, as far as it is capable of inhibiting either (1) the function of the p38 protein or (2) the expression of the p38 gene. That is, not only substances that act directly on the p38 protein to inhibit the function thereof and substances that act directly on the p38 gene to inhibit the expression thereof, but also substances that act on a factor involved in p38 signal transduction to result in inhibition of the function of the p38 protein or the expression of the p38 gene, are also included in the scope of "an inhibitor of p38 function" as mentioned herein.

Examples of substances that inhibit the function of the p38 protein include, but are not limited to, a chemical inhibitor of p38, a dominant negative mutant of p38 or a nucleic acid that encodes the same, an anti-p38 antagonist antibody or a nucleic acid that encodes the same, a substance that inhibits the p38 pathway, and the like. Preferably, a chemical inhibitor of p38 can be mentioned.

(1-1) Chemical Inhibitors of p38

Examples of the "chemical inhibitors of p38" to be used in the present invention include, but are not limited to, p38 inhibitors SB203580 (i.e., 4-(4-fluorophenyl)-2-(4-methylsulfinylphenyl)-5-(4-pyridyl)-1H-imidazole), and derivatives thereof, and SB202190 (i.e., 4-(4-fluorophenyl)-2-(4-hydroxyphenyl)-5-(4-pyridyl)imidazole) and derivatives thereof, that act as the ATP competitive inhibitor disclosed in WO 99/42592, SB239063 (i.e., trans-1-(4-Hydroxycyclohexyl)-4-(4-fluorophenyl)-5-(2-methoxypyrimidin-4-yl) imidazole) and derivatives thereof disclosed in Underwood et al. (*J Pharmacol Exp Ther.* 293, 281-288 (2000)), SB220025 and derivatives thereof disclosed in Jackson et al. (*J Pharmacol Exp Ther.* 284, 687-692 (1998)), PD169316 disclosed in Gallagher et al. (*Bioorg. Med. Chem.* 5, 49. (1997)), RPR200765A disclosed in Mclay et al. (*Bioorg Med. Chem.* 9, 537-554. (2001)), AMG-548, BIRB-796, SClO-469, SCIO-323 and VX-702 disclosed in Nikas et al. (*Curr Opin Drug Discov Devel.* 8, 421-430. (2005)), FR167653 disclosed in Yamamoto et al. (*Eur. J. Pharmacol.* 314, 137-142. (1996)) and the like. Preferred are SB202190, SB203580 and SB239063, and more preferred is SB202190. These are commercially available and, for example, SB203580, SB202190, SC239063, SB220025 and PD169316 are available from Calbiochem, and SClO-469 and SCIO-323 are available from Scios and the like.

Contact of a chemical inhibitor of p38 with a somatic cell can be performed by dissolving the inhibitor at an appropriate concentration in an aqueous or non-aqueous solvent, adding the solution of the inhibitor to a medium suitable for cultivation of somatic cells isolated from a human or mouse (for example, minimal essential medium (MEM), Dulbecco's modified Eagle medium (DMEM), RPMI1640 medium, 199 medium, F12 medium and the like supplemented with about 5 to 20% fetal bovine serum) so that the inhibitor concentration will fall in a range that fully inhibits the p38 function and does not cause cytotoxicity, and culturing the cells for a given period. The inhibitor concentration varies depending on the kind of inhibitor used, and is chosen as appropriate over the range of about 0.1 nM to about 100 nM. Duration of contact is not particularly limited, as far as it is sufficient to achieve nuclear reprogramming of the cells; usually, the inhibitor may be allowed to co-present in the medium until a positive colony emerges.

(1-2) Dominant Negative Mutants of p38

While p38 normally possesses phosphorylating activity as a kinase, "a dominant negative mutant of p38" as mentioned herein may be any substance that acts competitively against the wild p38 protein endogenous in somatic cells to inhibit the function thereof, without phosphorylating the substrate despite the capability of binding to the substrate. Examples of such substances include p38T180A, a mutant generated by a point mutation to replace the 180-position threonine in the DNA-binding region of p38 with alanine in humans and mice, p38Y182F, a mutant generated by a point mutation to replace the 182-position tyrosine in p38 with phenylalanine in humans and mice, and the like [Raingeaud J., *J Biol Chem*. 270, 7420-7426. (1995)].

A dominant negative mutant of p38 can be obtained by, for example, the technique described below. First, as for mouse p38, for example, an appropriate oligonucleotide is synthesized as a probe or primer on the basis of NM_011951 sequence of NCBI (SEQ ID NO:1) in the case of p38α, or NM_011161 (SEQ ID NO:3) in the case of p38β, as for human p38, NM_001315 sequence of NCBI (SEQ ID NO:2) in the case of p38α, and NM_002751 (SEQ ID NO:4) in the case of p38β, and a mouse or human p53 cDNA is cloned from a mRNA, cDNA or cDNA library derived from a mouse or human cell or tissue, using the hybridization method or the (RT-)PCR method, and is subcloned into an appropriate plasmid. In a form wherein a codon of the site into which a mutation is to be introduced is replaced with a codon that encodes another desired amino acid, a primer comprising the site is synthesized, and inverse PCR is performed using this primer with the plasmid incorporating the p38 cDNA as a template, whereby a nucleic acid that encodes the desired dominant negative mutant is acquired. In the case of a deletion mutant, a primer may be designed outside the site to be deleted, and inverse PCR may be performed as described above. By introducing the thus-obtained nucleic acid that encodes the dominant negative mutant into a host cell, and recovering a recombinant protein from a cell culture obtained by cultivating the cell, the desired dominant negative mutant can be acquired.

Contact of a dominant negative mutant with a somatic cell can be achieved using a method known per se for protein transfer into a cell. Such methods include, for example, the method using a protein transfer reagent, the method using a protein transfer domain (PTD)—or cell penetrating peptide (CPP)—fused protein, the microinjection method and the like. Protein transfer reagents are commercially available, including BioPOTER Protein Delivery Reagent (Gene Therapy Systems), Pro-Ject™ Protein Transfection Reagent (PIERCE) and ProVectin (IMGENEX), which are based on a cationic lipid; Profect-1 (Targeting Systems), which is based on a lipid; Penetrain Peptide (Q biogene) and Chariot Kit (Active Motif), which are based on a membrane-permeable peptide, GenomONE (ISHIHARA SANGYO KAISHA, LTD.) utilizing HVJ envelope (inactivated hemagglutinating virus of Japan) and the like. The transfer can be achieved per the protocols attached to these reagents, a common procedure being as described below. A dominant negative mutant of p38 is diluted in an appropriate solvent (for example, a buffer solution such as PBS or HEPES), a transfer reagent is added, the mixture is incubated at room temperature for about 5 to 15 minutes to form a complex, this complex is added to the cells after medium exchange with a serum-free medium, and the cells are incubated at 37° C. for one to several hours. Thereafter, the medium is removed and replaced with a serum-containing medium.

Developed PTDs include those using cell penetrating domains of a proteins, such as drosophila-derived AntP, HIV-derived TAT (Frankel, A. et al, *Cell* 55, 1189-93 (1988) or Green, M. & Loewenstein, P. M. *Cell* 55, 1179-88 (1988)), Penetratin (Derossi, D. et al, *J. Biol. Chem.* 269, 10444-50 (1994)), Buforin II (Park, C. B. et al. *Proc. Natl. Acad. Sci. USA* 97, 8245-50 (2000)), Transportan (Pooga, M. et al. *FASEB J.* 12, 67-77 (1998)), MAP (model amphipathic peptide) (Oehlke, J. et al. *Biochim. Biophys. Acta.* 1414, 127-39 (1998)), K-FGF (Lin, Y. Z. et al. *J. Biol. Chem.* 270, 14255-14258 (1995)), Ku70 (Sawada, M. et al. *Nature Cell Biol.* 5, 352-7 (2003)), Prion (Lundberg, P. et al. *Biochem. Biophys. Res. Commun.* 299, 85-90 (2002)), pVEC (Elmquist, A. et al. *Exp. Cell Res.* 269, 237-44 (2001)), Pep-1 (Morris, M. C. et al. *Nature Biotechnol.* 19, 1173-6 (2001)), Pep-7 (Gao, C. et al. *Bioorg. Med. Chem.* 10, 4057-65 (2002)), SynB1 (Rousselle, C. et al. *Mol. Pharmacol.* 57, 679-86 (2000)), HN-I (Hong, F. D. & Clayman, G L. *Cancer Res.* 60, 6551-6 (2000)), and HSV-derived VP22. CPPs derived from the PTDs include polyarginines such as 11R (*Cell Stem Cell*, 4, 381-384 (2009)) and 9R (*Cell Stem Cell*, 4, 472-476 (2009)).

A fusion protein expression vector incorporating a cDNA of a dominant negative mutant of p38 and a PTD or CPP sequence is prepared to allow recombinant expression of the fusion protein, and the fusion protein is recovered for use in the transfer. This transfer can be achieved as described above, except that no protein transfer reagent is added. It is preferable for the introduction of a deletion mutant having a relatively small molecular weight.

Microinjection, a method of placing a protein solution in a glass needle having a tip diameter of about 1 μm, and injecting the solution into a cell, ensures the transfer of the protein into the cell.

Other useful methods of protein transfer include electroporation, the semi-intact cell method [Kano, F. et al. *Methods in Molecular Biology*, Vol. 322, 357-365 (2006)], transfer using the Wr-t peptide [Kondo, E. et al., *Mol. Cancer Ther.* 3(12), 1623-1630 (2004)] and the like.

The protein transferring operation can be performed one or more optionally chosen times (e.g., once or more to 10 times or less, or once or more to 5 times or less and the like). Preferably, the transferring operation can be performed twice or more (e.g., 3 times or 4 times) repeatedly. The time interval for repeated transferring operation is, for example, 6 hours to 7 days, preferably 12 to 48 hours or 7 days.

(1-3) Nucleic Acids that Encode a Dominant Negative Mutant of p38

However, taking into account the ease of introduction into a somatic cell, a dominant negative mutant of p38 may be used in the form of a nucleic acid that encodes a protein, rather than of the protein itself. Therefore, in another preferred mode of embodiment of the present invention, the inhibitor of p38 function is a nucleic acid that encodes a dominant negative mutant of p38. The nucleic acid may be a DNA or an RNA, or a DNA/RNA chimera, and is preferably a DNA. The nucleic acid may be double-stranded or single-stranded. A cDNA that encodes a dominant negative mutant of p38 can be cloned by the technique described above with respect to preparation of the mutant protein.

The cDNA isolated is inserted into an appropriate expression vector comprising a promoter capable of functioning in a target somatic cell. Useful expression vectors include, for example, viral vectors such as retrovirus, lentivirus, adenovirus, adeno-associated virus, Sendai virus and herpesvirus, plasmids for the expression in animal cells (e.g., pA1-11, pXT1, pRc/CMV, pRc/RSV, pcDNAI/Neo) and the like. A m kind of vector used can be chosen as appropriate according to the intended use of the iPS cells obtained.

Useful promoters used in the expression vector include, for example, EF1α promoter, CAG promoter, SRα promoter, SV40 promoter, LTR promoter, CMV (cytomegalovirus) promoter, RSV (Rous sarcoma virus) promoter, MoMuLV (Moloney mouse leukemia virus) LTR, HSV-TK (herpes simplex virus thymidine kinase) promoter and the like. Preference is given to EF1α promoter, CAG promoter, MoMuLV LTR, CMV promoter, SRα promoter and the like.

The expression vector may harbor, as desired, in addition to a promoter, an enhancer, a polyadenylation signal, a selectable marker gene, an SV40 replication origin and the like. Examples of the selectable marker gene include the dihydrofolate reductase gene, the neomycin resistance gene and the like.

A nucleic acid that encodes a dominant negative mutant of p38 may be integrated alone into an expression vector, or along with one or more reprogramming genes into an expression vector. Preference is sometimes given to the former case when using a retrovirus or lentivirus vector, which offers high gene transfer efficiency, and to the latter case when using a plasmid, adenovirus, or episomal vector and the like, but there are no particular limitations.

In the context above, when a nucleic acid that encodes a dominant negative mutant of p38 and one or more reprogramming genes are integrated in one expression vector, these genes can preferably be integrated into the expression vector via a sequence enabling polycistronic expression. By using a sequence enabling polycistronic expression, it is possible to more efficiently express a plurality of genes integrated in one expression vector. Useful sequences enabling polycistronic expression include, for example, the 2A sequence of foot-and-mouth disease virus (*PLoS ONE* 3, e2532, 2008, *Stem Cells* 25, 1707, 2007), the IRES sequence (U.S. Pat. No. 4,937,190) and the like, with preference given to the 2A sequence.

An expression vector harboring a nucleic acid encoding a dominant negative mutant of p38 can be introduced into a cell by a technique known per se according to the kind of the vector. In the case of a viral vector, for example, a plasmid containing the nucleic acid encoding a dominant negative mutant is introduced into an appropriate packaging cell (e.g., Plat-E cells) or a complementary cell line (e.g., 293-cells), the viral vector produced in the culture supernatant is recovered, and the vector is infected to the cell by a method suitable for the viral vector. For example, specific means using a retroviral vector as a vector are disclosed in WO2007/69666, *Cell*, 126, 663-676 (2006) and *Cell*, 131, 861-872 (2007); when a lentiviral vector is used as a vector, a disclosure is available in *Science*, 318, 1917-1920 (2007). When iPS cells are utilized as a source of cells for regenerative medicine, the expression (reactivation) of a dominant negative mutant of p38 or the activation of an endogenous gene present in the vicinity of the site where the exogenous gene is integrated potentially increases the risk of carcinogenesis in tissues regenerated from differentiated cells of iPS cell derivation; therefore, a nucleic acid that encodes a dominant negative mutant of p38 is preferably expressed transiently, without being integrated into the chromosome of the cells. From this viewpoint, use of an adenoviral vector, whose integration into chromosome is rare, is preferred. Specific means using an adenoviral vector is described in *Science*, 322, 945-949 (2008). Because an adeno-associated viral vector is also low in the frequency of integration into chromosome, and is lower than adenoviral vectors in terms of cytotoxicity and inflammation-inducibility, it can be mentioned as another preferred vector. Because Sendai viral vector is capable of being stably present outside the chromosome, and can be degraded and removed using an siRNA as required, it is preferably utilized as well. Regarding a Sendai viral vector, one described in *J. Biol. Chem.*, 282, 27383-27391 (2007) and JP-3602058 B can be used.

When a retroviral vector or a lentiviral vector is used, even if silencing of the transgene has occurred, it possibly becomes reactivated later; therefore, for example, a method can be used preferably wherein a nucleic acid that encodes a dominant negative mutant of p38 is cut out using the Cre/loxP system, when becoming unnecessary. That is, with loxP sequences arranged on both ends of the nucleic acid in advance, after iPS cells are induced, the Cre recombinase is allowed to act on the cells using a plasmid vector or adenoviral vector, and the region sandwiched by the loxP sequences can be cut out. Because the enhancer-promoter sequence of the LTR U3 region possibly upregulates a host gene in the vicinity thereof by insertion mutation, it is more preferable to avoid the expression regulation of the endogenous gene by the LTR outside of the loxP sequence remaining in the genome without being cut out, using a 3'-self-inactivating (SIN) LTR prepared by deleting the sequence, or substituting the sequence with a polyadenylation sequence such as of SV40. Specific means using the Cre/loxP system and SIN LTR is disclosed in Soldner et al., *Cell*, 136: 964-977 (2009), Chang et al., *Stem Cells*, 27: 1042-1049 (2009) and the like.

Meanwhile, in the case of a plasmid vector, which is a non-viral vector, the vector can be introduced into a cell using the lipofection method, liposome method, electroporation method, calcium phosphate co-precipitation method, DEAE dextran method, microinjection method, gene gun method and the like. A specific means using a plasmid as a vector is described in, for example, *Science*, 322, 949-953 (2008) and the like.

When a plasmid vector, an adenovirus vector and the like are used, the transfection can be performed once or more optionally chosen times (e.g., once to 10 times, once to 5 times or the like). When two or more kinds of expression vectors are introduced into a somatic cell, it is preferable that these all kinds of expression vectors be concurrently introduced into a somatic cell; however, even in this case, the transfection can be performed once or more optionally chosen times (e.g., once to 10 times, once to 5 times or the like), preferably the transfection can be repeatedly performed twice or more (e.g., 3 times or 4 times).

Also when an adenovirus or a plasmid is used, the transgene can get integrated into chromosome; therefore, it is eventually necessary to confirm the absence of insertion of the gene into chromosome by Southern blotting or PCR. For this reason, like the aforementioned Cre/loxP system, it can be advantageous to use a means wherein the transgene is integrated into chromosome, thereafter the gene is removed. In another preferred mode of embodiment, a method can be used wherein the transgene is integrated into chromosome using a transposon, thereafter a transposase is allowed to act on the cell using a plasmid vector or adenoviral vector so as to completely eliminate the transgene from the chromosome. As examples of preferable transposons, piggyBac, a transposon derived from a lepidopterous insect, and the like can be mentioned. Specific means using the piggyBac transposon is disclosed in Kaji, K. et al., *Nature*, 458: 771-775 (2009), Woltjen et al., *Nature*, 458: 766-770 (2009).

Another preferable non-integration type vector is an episomal vector, which is autonomously replicable outside the chromosome. Specific means with the use of an episomal vector is described by Yu et al. in *Science*, 324, 797-801 (2009), *Nature Methods*, 8(5), 409-412 (2011) and WO 2011/016588. As appropriate, an expression vector in which a nucleic acid that encodes a dominant negative mutant of p38 is inserted into an episomal vector having loxP sequences placed in the same orientation on the 5' and 3' sides of the vector constituent essential for the replication of the episomal vector can be constructed and introduced into a somatic cell.

Examples of the episomal vector include a vector comprising as a vector component a sequence derived from EBV, SV40 and the like necessary for self-replication. The vector component necessary for self-replication is specifically exemplified by a replication origin and a gene that encodes a protein that binds to the replication origin to control the replication; examples include the replication origin oriP and the EBNA-1 gene for EBV, and the replication origin on and the SV40 large T antigen gene for SV40. Alternatively, the S/MAR sequence from the pEPI-based vectors or α-satellite DNA for a human artificial chromosome can also be used as a vector component necessary for self-replication (*Mol Ther* 16(9), 1525-1538 (2008)).

The episomal expression vector harbors a promoter that controls the transcription of a nucleic acid that encodes a dominant negative mutant of p38. Useful promoters include those mentioned above. The episomal expression vector, like the aforementioned vectors, may further contain as desired an enhancer, a polyadenylation signal, a selectable marker gene and the like. Examples of useful selectable marker genes include the dihydrofolate reductase gene, the neomycin-resistant gene and the like.

The loxP sequences useful in the present invention include, in addition to the bacteriophage P1-derived wild type loxP sequence, optionally chosen mutant loxP sequences capable of deleting the sequence flanked by the loxP sequence by recombination when placed in the same orientation at positions flanking a vector component necessary for the replication of the introduced gene. Examples of such mutant loxP sequences include lox71, mutated in 5' repeat, lox66, mutated in 3' repeat, and lox2272 and lox511, mutated in spacer portion. Although the two loxP sequences placed on the 5' and 3' sides of the vector component may be identical or not, the two mutant loxP sequences mutated in spacer portion must be identical (e.g., a pair of lox2272 sequences, a pair of lox511 to sequences). Preference is given to a combination of a mutant loxP sequence mutated in 5' repeat (e.g., lox71) and a mutant loxP sequence mutated in 3' repeat (e.g., lox66). In this case, the loxP sequences remaining on the chromosome have double mutations in the repeats on the 5' side and 3' side as a result of recombination, and are therefore unlikely to be recognized by Cre recombinase, thus reducing the risk of causing a deletion mutation in the chromosome due to unwanted recombination. When the mutant loxP sequences lox71 and lox66 are used in combination, each may be placed on any of the 5' and 3' sides of the aforementioned vector component, but it is necessary that the mutant loxP sequences be inserted in an orientation such that the mutated sites would be located at the outer ends of the respective loxP sequences. Although a preferred episomal vector of the present invention is a self-removal vector early shedding from the cell even without being acted on by Cre recombinase, there are possibly exceptional cases where longer time is taken for the episomal vector to be shed from the cell. It is preferable, therefore, that the loxP sequences be designed in preparation for risks such as unwanted recombination due to Cre recombinase treatment.

Each of the two loxP sequences is placed in the same orientation on the 5' and 3' sides of a vector constituent essential for the replication of the introduced gene (i.e., a replication origin, or a gene sequence that encodes a protein that binds to the replication origin to control the replication). The vector constituent flanked by the loxP sequences may be either the replication origin or a gene sequence that encodes a protein that binds to a replication origin to control the replication, or both.

The episomal vector allows the vector to be introduced into the cell using, for example, the lipofection method, liposome method, electroporation method, calcium phosphate co-precipitation method, DEAE dextran method, microinjection method, gene gun method and the like. Specifically, for example, methods described in *Science*, 324: 797-801 (2009), *Nature Methods*, 8(5), 409-412 (2011), WO 2011/016588 and elsewhere can be used.

Whether or not the vector component necessary for the replication of the introduced gene has been removed from the iPS cell can be confirmed by performing a Southern blot analysis or PCR analysis using a nucleic acid comprising a nucleotide sequence in the vector component as a probe or primer, with the episome fraction isolated from the iPS cell as a template, and determining the presence or absence of a band or the length of the band detected. The episome fraction can be prepared by a method well known in the art; for example, methods described in *Science*, 324: 797-801 (2009), *Nature Methods*, 8(5), 409-412 (2011), WO 2011/016588 and elsewhere can be used.

(1-4) Inhibitors of p38 Pathway

Here, the term p38 pathway is used with a meaning including all upstream signal transduction pathways that can activate p38 and all downstream signal transduction pathways mediated by activated p38. Therefore, inhibitors of p38 pathway include all substances that inhibit any one of the aforementioned signal transduction pathways. Regarding the p38 signaling pathway, it is known that upon stimulation by stress or inflammatory cytokines such as IL-1 and TNFα, MAPKKK (MAP kinase) molecules such as ASK1, TAK1, and MLK3 get activated to phosphorylate the MAPKK (MAP kinase) molecules MKK3/6 and MKK4 and hence activate p38 as an MAPK (MAP kinase). For example, the TNFα inhibitor infliximab (Centcore) is available, as an inflammatory cytokine inhibitor upstream of the p38 pathway. Also included are substances that inhibit the expression or function of other upstream molecule MKK3/6 (e.g., dominant negative mutants, siRNAs, and shRNAs against these factors) and the like. Publicly known anti-MKK3/6 siRNAs include, for example, SC-43924 (Santa Cruz Biotechnology).

Downstream of p38 are present MAPKAPK2/K3, ATF-2, HSP27 and other transcription factors, where p38 works as a regulator of the gene expression. Still also included are substances that inhibit the expression or function thereof (e.g., dominant negative mutants, siRNAs, and shRNAs against these factors) and the like. For example, publicly known MAPKAPK2 inhibitors include Hsp25 Kinase Inhibitor (Calbiochem) and the like.

(1-5) Other Substances

As examples of other substances that inhibit the function of the p38 protein, anti-p38 antagonist antibody or a nucleic acid that encodes the same can be mentioned. The anti-p38 antagonist antibody may be a polyclonal antibody or a monoclonal antibody. The isotype of the antibody is not particularly limited, and is preferably IgG, IgM or IgA, particularly preferably IgG. The antibody may be, in addition to a complete antibody molecule, for example, a fragment such as Fab, Fab', or F(ab')$_2$, a conjugate molecule prepared by a gene engineering technique, such as scFv, scFv-Fc, minibody, or diabody, or a derivative thereof modified with a molecule having protein-stabilizing action, such as polyethylene glycol (PEG). An anti-p38 antagonist antibody can be produced using p38 or a partial peptide thereof as an antigen, by a method of antibody or anti-serum production known per se. As known anti-p38 antagonist antibody, for example, SC-728 (Santa Cruz Biotechnology), 9212 (Cell Signaling Technology) and the like can be mentioned. A nucleic acid that encodes an anti-p38 antagonist antibody can be isolated from a hybridoma that produces an anti-p38 monoclonal antibody by a conventional method. The H-chain and L-chain genes obtained may be joined together to prepare a nucleic acid that encodes a single-chain antibody.

An anti-p38 antagonist antibody, or a nucleic acid that encodes the antibody can be introduced into a cell with the method described in the statement of a dominant negative mutant of p38 or a nucleic acid that encodes the mutant, respectively.

Meanwhile, as examples of substances that inhibit the expression of the p38 gene, siRNAs or shRNAs against p38, vectors that express an siRNA or shRNA against p38, antisense nucleic acids against p38 and ribozymes against p38, and the like can be mentioned.

(2-1) siRNA and shRNA Against p38

An siRNA against each p38 can be designed on the basis of the mouse or human p38 cDNA sequence information shown by SEQ ID NO:1 to 4, in accordance with, for example, the rules proposed by Elbashir et al. (*Genes Dev.*, 15, 188-200 (2001)). The target sequence for the siRNA is, as a general rule, AA+(N)$_{19}$, but may be AA+(N)$_{21}$ or NA+(N)$_{21}$. The 5' end of the sense strand need not to be AA. Although the position of the target sequence is not particularly limited, it is desirable that the target sequence be selected between 5'-UTR and about 50 bases from the start codon, as well as from a region other than 3'-UTR. The GC content of the target sequence is also not particularly limited, but the content is preferably about 30 to about 50%; a sequence with no irregularity in GC distribution and with only a few repeats is desirable. When a polIII promoter is used as a promoter in designing a vector that expresses an siRNA or shRNA of (2-2) below, a sequence with 4 or more T or A bases in succession should not be chosen, so as to prevent polymerase transcription from ceasing.

The target sequence candidates selected on the basis of the above-described rules are examined for homology to sequences of 16-17 bases in succession in mRNAs other than the target, using a homology search software program such as BLAST (http://www.ncbi.nlm.nih.gov/BLAST/), so as to confirm the specificity of the target sequences selected. For the target sequences for which the specificity has been confirmed, a double-stranded RNA consisting of a sense strand having a 3'-terminal overhang of TT or UU in 19-21 bases after AA (or NA) and, and an antisense strand having a sequence complementary to the 19-21 bases and a 3'-terminal overhang of TT or UU, is designed as an siRNA. Also, an shRNA can be designed by choosing as appropriate an optionally chosen linker sequence capable of forming a loop structure (for example, about 8-25 bases), and ligating the aforementioned sense strand and antisense strand via the linker sequence.

Sequences of siRNAs and/or shRNAs can be searched for using search software programs available at no cost on various websites. Examples of such sites include, but are not limited to, the siRNA Target Finder (http://www.ambion.com/jp/techlib/misc/siRNA_finder.html) and insert design tool for pSilencer™ Expression Vector (http://www.ambion.com/jp/techlib/misc/psilencer_converter.html), both provided by Ambion, and GeneSeer (http://codex.cshl.edu/scripts/newsearchhairpin.cgi), provided by RNAi Codex; and similar search is possible on the websites of QIAGEN, Takara Bio, SiSearch, Dharmacon, Whitehead Institute, Invitrogen, Promega and the like.

An siRNA against p38 can be prepared by synthesizing a sense strand oligonucleotide and antisense strand oligonucleotide designed as described above using an automated DNA/RNA synthesizer, respectively, and, for example, denaturing the oligonucleotides in an appropriate annealing buffer solution at about 90 to about 95° C. for about 1 minute, thereafter annealing the same at about 30 to about 70° C. for about 1 to about 8 hours. An shRNA against p38 can be prepared by synthesizing oligonucleotides having an shRNA sequence, designed as described above, using an automated DNA/RNA synthesizer, and allowing the same to self-anneal as described above.

Although the nucleotide molecules that constitute the siRNA and shRNA may be naturally occurring RNAs, the molecules can comprise various chemical modifications in order to increase the stability (chemical and/or to-enzyme) or specific activity (affinity for mRNA). For example, to prevent degradation by hydrolases such as nuclease, the phosphoric acid residue (phosphate) of each nucleotide that constitutes the antisense nucleic acid can be substituted with, for example, a chemically modified phosphoric acid residue such as phosphorothioate (PS), methylphosphonate, or phosphorodithionate. The hydroxyl group at the 2'-position of the sugar (ribose) of each nucleotide may be replaced with —OR (R represents, for example, CH$_3$(2'—O-Me), CH$_2$CH$_2$OCH$_3$(2'—O-MOE) CH$_2$CH$_2$NHC(NH)NH$_2$, CH$_2$CONHCH$_3$, CH$_2$CH$_2$CN or the like). Furthermore, a base moiety (pyrimidine, purine) may be chemically modified; for example, introduction of a methyl group or a cationic functional group into the 5-position of the pyrimidine base, substitution of the 2-position carbonyl group with thiocarbonyl and the like can be mentioned.

Regarding the conformation of the sugar moiety of RNA, two types are dominant: C2'-endo (S type) and C3'-endo (N type); in a single-stranded RNA, the sugar moiety occurs in an equilibrium of both, but when a double strand is formed, the conformation is fixed at the N type. Therefore, BNA (LNA) (Imanishi, T. et al., *Chem. Commun.*, 1653-9, 2002; Jepsen, J. S. et al., *Oligonucleotides*, 14, 130-46, 2004) and ENA (Morita, K. et al., *Nucleosides Nucleotides Nucleic Acids*, 22, 1619-21, 2003), which are RNA derivatives wherein the conformation of the sugar moiety is fixed at the N type by bridging the 2' oxygen and 4' carbon so as to confer strong bindability to the target RNA, can also be used preferably.

However, because replacing all ribonucleoside molecules in a naturally occurring RNA with modified type molecules can lead to the loss of RNAi activity, it is necessary to introduce a nucleoside modified to the minimum possible extent that allows the RISC complex to function.

siRNA against p38 can also be purchased from, for example, Santa Cruz (e.g., Santa Cruz Cat# sc-29433, sc-29434, sc-44216), Sigma Aldrich (e.g., SHGLY-NM_011951) and the like.

Contact of an siRNA or shRNA against p38 with a somatic cell can be achieved by, as in the case of plasmid DNA, introducing the nucleic acid into the cell using the liposome method, polyamine method, electroporation method, beads method and the like. The method using a cationic liposome is the most common and offers high transfer efficiency. In addition to common transfection reagents such as Lipofectamine2000 and Oligofectamine (Invitrogen), for example, transfer reagents suitable for introduction of an siRNA, such as the GeneEraser™ siRNA transfection reagent (Stratagene), are also commercially available.

(2-2) Vectors that Express siRNA or shRNA Against p38

Vectors that express an siRNA are available in the tandem type and the stem loop (hairpin) type. The former is the type in which an expression cassette for a sense strand of an siRNA and an expression cassette for an antisense strand are tandemly ligated, each strand being expressed in the cell and undergoing annealing to form a double-stranded siRNA (dsRNA). Meanwhile, the latter is the type in which an expression cassette for an shRNA is inserted into a vector, the shRNA being expressed in the cell and undergoing processing by a dicer to form a dsRNA. Although a polII promoter (for example, immediate-early promoter of CMV) may be used as the promoter, it is common practice to use a polIII promoter in order to allow the accurate transcription of short RNA. As the polIII promoter, mouse and human U6-snRNA promoters, human H1-RNase P RNA promoter, human valine-tRNA promoter and the like can be mentioned. As a transcription termination signal, a sequence of 4 or more T residues in succession is used.

The siRNA or shRNA expression cassette thus constructed is then inserted into a plasmid vector or a viral vector. As such vectors, the same as those described with respect to a nucleic acid that encodes a dominant negative mutant of p38 can be utilized preferably (viral vectors such as retrovirus, lentivirus, adenovirus, adeno-associated virus, Sendai virus and herpesvirus; animal cell expression plasmids and the like). The vector used can be chosen as appropriate according to the intended use of the iPS cell obtained, as in the case of a dominant negative mutant. Alternatively, as an expression vector that encodes an shRNA against p38, a viral vector such as retrovirus, prepared on the basis of a commercially available plasmid (for example, p38α shRNA Plasmid: sc-29434-SH, commercially available from Santa Cruz Biotechnology, and the like) or the like can also be used.

Contact of a vector that expresses an siRNA or shRNA against p38 with a somatic cell is achieved by introducing a plasmid vector or viral vector prepared as described above into the cell. Transfer of these genes can be achieved by the same technique as that described with respect to a nucleic acid that encodes a dominant negative mutant of p38.

(2-3) Other Substances

As other substances that inhibit the expression of the p38 gene, antisense nucleic acids against p38 and ribozymes can be mentioned.

The antisense nucleic acid may be a DNA or an RNA, or a DNA/RNA chimera. When the antisense nucleic acid is a DNA, an RNA:DNA hybrid formed by a target RNA and the antisense DNA is capable of being recognized by endogenous RNase H to cause selective degradation of the target RNA. Therefore, in the case of an antisense DNA to be degraded with RNase H, the target sequence may be not only a sequence in p38 mRNA, but also a sequence in the intron region of the primary transcript of the p38 gene. The length of the target region for the antisense nucleic acid is not particularly limited, as far as hybridization of the antisense nucleic acid results in an inhibition of the translation into the p38 protein; the target region may be the entire sequence or a partial sequence of p38 mRNA, and may be a sequence of about 15 bases for the shortest, or of the entire sequence of the mRNA or primary transcript for the longest. Considering the ease of synthesis, antigenicity, transferability in cells and other issues, an oligonucleotide consisting of about 15 to about 40 bases, particularly about 18 to about 30 bases, is preferable. Positions of the target sequence include, but are not limited to, 5'- and 3'-UTR, vicinities of the start codon and the like.

A ribozyme refers to an RNA possessing an enzyme activity to cleave a nucleic acid in the narrow sense, and is herein understood to be used as a concept encompassing a DNA, as far as the ribozyme possesses sequence-specific nucleic acid cleavage activity. One of the most versatile ribozymes is a self-splicing RNA found in infectious RNAs such as viroid and virusoid, and the hammerhead type, the hairpin type and the like are known. The hammerhead type exhibits enzyme activity with about 40 bases in length, and it is possible to specifically cleave the target mRNA by making several bases at both ends adjoining to the hammerhead structure portion (about 10 bases in total) be a sequence complementary to the desired cleavage site of the mRNA.

An antisense nucleic acid or a ribozyme can be synthesized using an automated DNA/RNA synthesizer. The nucleotide molecules that constitute them may also have the same modifications as those for siRNA, so as to increase the stability, specific activity and the like.

Alternatively, the antisense nucleic acid or ribozyme can also be used in the form of a nucleic acid that encodes the same, as in the case of siRNA.

The aforementioned inhibitor of p38 function needs to be brought into contact with a somatic cell in a way sufficient to inhibit the p38 function in the step of somatic cell nuclear reprogramming. Here, nuclear reprogramming of the somatic cell can be achieved by bringing a nuclear reprogramming substance into contact with the somatic cell.

(c) Nuclear Reprogramming Substances

In the present invention, "a nuclear reprogramming substance" may be consisted of any substance as long as it is a substance (group) capable of inducing an iPS cell from a somatic cell by introduction thereof into the somatic cell, such as a proteinous factor or a nucleic acid that encodes the same (including forms incorporated in a vector), or a low-molecular compound. When the nuclear reprogramming substance is a proteinous factor or a nucleic acid that encodes the same, the following combinations can be mentioned as preferable examples (hereinafter, only the names for proteinous factors are shown).

(1) Oct3/4, Klf4, c-Myc
(2) Oct3/4, Klf4, c-Myc, Sox2 (here, Sox2 is replaceable with Sox1, Sox3, Sox15, Sox17 or Sox18. Also, Klf4 is replaceable with Klf1, Klf2 or Klf5. Furthermore, c-Myc is replaceable with T58A (active mutant), N-Myc, L-Myc.)
(3) Oct3/4, Klf4, c-Myc, Sox2, Fbx15, Nanog, Eras, ECAT15-2, Tcl1, β-catenin (active mutant S33Y)
(4) Oct3/4, Klf4, c-Myc, Sox2, TERT, SV40 Large T antigen (hereinafter, SV40LT)
(5) Oct3/4, Klf4, c-Myc, Sox2, TERT, HPV16 E6
(6) Oct3/4, Klf4, c-Myc, Sox2, TERT, HPV16 E7
(7) Oct3/4, Klf4, c-Myc, Sox2, TERT, HPV6 E6, HPV16 E7
(8) Oct3/4, Klf4, c-Myc, Sox2, TERT, Bmil
(for all above, see WO 2007/069666 (however, in the combination (2) above, for replacement of Sox2 with Sox18, and replacement of Klf4 with Klf1 or Klf5, see *Nature Biotechnology*, 26, 101-106 (2008)). For combinations of "Oct3/4, Klf4, c-Myc, Sox2", see also *Cell*, 126, 663-676 (2006), Cell, 131, 861-872 (2007) and the like. For combinations of "Oct3/4, Klf2 (or Klf5), c-Myc, Sox2", see also *Nat. Cell Biol.*, 11, 197-203 (2009). For combinations of "Oct3/4, Klf4, c-Myc, Sox2, hTERT, SV40LT", see also *Nature*, 451, 141-146 (2008).)

(9) Oct3/4, Klf4, Sox2 (see *Nature Biotechnology*, 26, 101-106 (2008))
(10) Oct3/4, Sox2, Nanog, Lin28 (see *Science*, 318, 1917-1920 (2007))
(11) Oct3/4, Sox2, Nanog, Lin28, hTERT, SV40LT (see *Stem Cells*, 26, 1998-2005 (2008))
(12) Oct3/4, Klf4, c-Myc, Sox2, Nanog, Lin28 (see *Cell Research* (2008) 600-603)
(13) Oct3/4, Klf4, c-Myc, Sox2, SV40LT (see also *Stem Cells*, 26, 1998-2005 (2008))
(14) Oct3/4, Klf4 (see *Nature* 454:646-650 (2008), Cell Stem Cell, 2:525-528 (2008)))
(15) Oct3/4, c-Myc (see *Nature* 454:646-650 (2008))
(16) Oct3/4, Sox2 (see Nature, 451, 141-146 (2008), WO2008/118820)
(17) Oct3/4, Sox2, Nanog (see WO2008/118820)
(18) Oct3/4, Sox2, Lin28 (see WO2008/118820)
(19) Oct3/4, Sox2, c-Myc, Esrrb (here, Esrrb is replaceable with Esrrg; see Nat. Cell Biol., 11, 197-203 (2009))
(20) Oct3/4, Sox2, Esrrb (see *Nat. Cell Biol.*, 11, 197-203 (2009))
(21) Oct3/4, Klf4, L-Myc
(22) Oct3/4, Nanog
(23) Oct3/4 (*Cell* 136: 411-419 (2009),*Nature*, 08436, doi: 10.1038 published online (2009))
(24) Oct3/4, Klf4, c-Myc, Sox2, Nanog, Lin28, SV40LT (see *Science*, 324: 797-801 (2009))

In (1)-(24) above, in place of Oct3/4, other members of the Oct family, for example, Oct1A, Oct6 and the like, can also be used. In place of Sox2 (or Sox1, Sox3, Sox15, Sox17, Sox18), other members of the Sox family, for example, Sox7 and the like, can also be used. In place of Klf4, other members of the Klf family, for example, Klf1, Klf2 and Klf5, or known Klf4 substitutes, for example, members of the Esrr family such as Esrrb, Esrrg and the like, members of the IRX family such as IRX1, IRX2, IRX3, IRX4, IRX5, IRX6 and the like, members of the GLIS family such as GLIS1, GLIS2, GLIS3 and the like, members of the PTX family such as PITX1, PITX2, PITX3 and the like, and DMRTB1 can also be used. Furthermore, in (1) to (24) above, when c-Myc or Lin28 is included as a nuclear reprogramming factor, L-Myc or Lin28B can be used in place of c-Myc or Lin28, respectively. Members of the GLIS family such as GLIS1 may also be used in place of c-Myc.

Any combination that does not fall in (1)-(24) above, but contains all the constituents in any one thereof and further comprises an optionally chosen other substance, can also be included in the scope of "nuclear reprogramming substances" in the present invention. Under conditions wherein the somatic cell being the subject of nuclear reprogramming is endogenously expressing a part of the constituents in any one of (1)-(24) above at a level sufficient to secure nuclear reprogramming, a combination of the remaining constituents excluding the constituents can also be included in the scope of "nuclear reprogramming substances" in the present invention.

Among these combinations, at least one, preferably two or more, more preferably three or more selected from Oct3/4, Sox2, Klf4, c-Myc or L-Myc, Nanog, Lin28 or Lin28B and GLIS1 can be mentioned as examples of preferable nuclear reprogramming substance.

Particularly, with the use of the iPS cells obtained for therapeutic purposes in mind, the combination of the 3 factors Oct3/4, Sox2 and Klf4 (that is, (9) above) is preferable. Meanwhile, when the use of the iPS cells for therapeutic purposes is not in mind (for example, used as an investigational tool for drug discovery screening and the like), 3 factors of Oct3/4, Sox2 and Klf4, as well as 4 factors additionally further containing c-Myc/L-Myc, 5 factors additionally further containing Lin28/Lin28B, 6 factors additionally further containing GLIS1, 7 factors additionally further containing Nanog, and the like can be recited as examples.

Mouse and human cDNA sequence information on the aforementioned proteinous factors can be acquired by referring to the NCBI accession numbers mentioned in WO 2007/069666 (in the publication, Nanog is mentioned with the designation "ECAT4"; mouse and human cDNA sequence information on L-Myc, Lin28, Lin28B, GLIS1, Esrrb and Esrrg can be acquired by referring to the following NCBI accession numbers, respectively); those skilled in the art are easily able to isolate these cDNAs.

| Name of gene | Mouse | Human |
| --- | --- | --- |
| L-Myc | NM_008506 | NM_001033081 |
| Lin28 | NM_145833 | NM_024674 |
| Lin28b | NM_001031772 | NM_001004317 |
| Glis1 | NM_147221 | NM_147193 |
| Esrrb | NM_011934 | NM_004452 |
| Esrrg | NM_011935 | NM_001438 |

When a proteinous factor itself is used as a nuclear reprogramming substance, the factor can be prepared by inserting the cDNA obtained into an appropriate expression vector, introducing the vector into a host cell, culturing the cell, and recovering the recombinant proteinous factor from the culture obtained. Meanwhile, when a nucleic acid that encodes a proteinous factor is used as a nuclear reprogramming substance, the cDNA obtained is inserted into a viral vector, an episomal vector or a plasmid vector to construct an expression vector as in the aforementioned case of a nucleic acid that encodes a dominant negative mutant of p38, and the vector is subjected to the step of nuclear reprogramming. The Cre-loxP system or piggyBac transposon system can be utilized as required. When 2 or more nucleic acids that encode a proteinous factor are introduced into a cell as nuclear reprogramming substances, the nucleic acids may be carried by separate vectors, and a plurality of nucleic acids may be joined tandem to obtain a polycistronic vector. In the latter case, to enable efficient polycistronic expression, it is desirable that the 2A self-cleaving peptide of foot-and-mouth disease virus be ligated between the individual nucleic acids (see *Science*, 322, 949-953, 2008 and the like).

Contact of a nuclear reprogramming substance with a somatic cell can be achieved as with the aforementioned dominant negative mutant of p38 (a) when the substance is a proteinous factor; as with the aforementioned nucleic acid that encodes a dominant negative mutant of p38 (b) when the substance is a nucleic acid that encodes the proteinous factor (a); and as with the aforementioned chemical inhibitor of p38 (c) when the nuclear programming substance is a low-molecular compound.

(d) iPS Cell Establishment Efficiency Improvers

By bringing, in addition to the above-mentioned inhibitor of p38 function, another publicly known iPS cell establishment efficiency improver, into contact with a somatic cell, the efficiency of establishment of iPS cells is expected to be increased more.

Examples of iPS cell establishment efficiency improvers include, but are not limited to, histone deacetylase (HDAC) inhibitors [e.g., valproic acid (VPA) (*Nat. Biotechnol.*, 26(7): 795-797 (2008)), low-molecular inhibitors such as trichostatin A, sodium butyrate; MC 1293, and M344, nucleic acid-based expression inhibitors such as siRNAs and shRNAs against HDAC (e.g., HDAC1 siRNA Smartpool® (Millipore), HuSH 29 mer shRNA Constructs against HDAC1 (OriGene) and the like), and the like], DNA methyl transferase inhibitors (for example, 5'-azacytidine) (Nat. Biotechnol., 26(7): 795-797 (2008)), G9a histone methyl transferase inhibitors [for example, low-molecular inhibitors such as BIX-01294 (Cell Stem Cell, 2: 525-528 (2008)) and the like, nucleic acid-based expression inhibitors such as siRNAs and shRNAs against G9a (e.g., G9a siRNA (human) (Santa Cruz Biotechnology) and the like) and the like], L-channel calcium agonists (for example, Bayk8644) (Cell Stem Cell, 3, 568-574 (2008)), p53 inhibitors (for example, siRNA and shRNA against p53 (Cell Stem Cell, 3, 475-479 (2008)), UTF1 (Cell Stem Cell, 3, 475-479 (2008)), Wnt signaling activator (for example, soluble Wnt3a) (Cell Stem Cell, 3, 132-135 (2008)), 2i/LIF (2i is an inhibitor of mitogen-activated protein kinase signaling and glycogen synthase kinase-3, PloS Biology, 6(10), 2237-2247 (2008)), ES cell-specific miRNA (for example, miR-302-367 cluster (Mol. Cell. Biol. doi:10.1128/MCB.00398-08), miR-302 (RNA (2008) 14: 1-10), miR-291-3p, miR-294 and miR-295 (for above, Nat. Biotechnol. 27: 459-461 (2009))), 3'-phosphoinositide-dependent kinase-1 (PDK1) acitvator (for example, PS48 (Cell Stem Cell, 7: 651-655 (2010)) and the like. As mentioned above, the nucleic acid-based expression inhibitors may be in the form of expression vectors harboring a DNA that encodes an siRNA or shRNA.

Of the aforementioned constituents of nuclear reprogramming substances, SV40 large T and the like, for example, can also be included in the scope of iPS cell establishment efficiency improvers because they are auxiliary factors unessential for the nuclear reprogramming of somatic cells. While the mechanism of nuclear reprogramming remains unclear, it does not matter whether auxiliary factors, other than the factors essential for nuclear reprogramming, are deemed nuclear reprogramming substances, or deemed iPS cell establishment efficiency improvers. Hence, because the somatic cell nuclear reprogramming process is visualized as an overall event resulting from contact of nuclear reprogramming substances and an iPS cell establishment efficiency improver with somatic cells, it does not always seem necessary for those skilled in the art to distinguish both.

Contact of these other iPS cell establishment efficiency improvers with a somatic cell can be achieved as described above with respect to inhibitors of p38 function, respectively, when the improver is (a) a proteinous factor, (b) a nucleic acid that encodes the proteinous factor, or (c) a low-molecular compound.

(e) Improving the Establishment Efficiency by Culture Conditions iPS cell establishment efficiency can further be improved by culturing the cells under hypoxic conditions in the nuclear reprogramming process for somatic cells. As mentioned herein, the term "hypoxic conditions" means that the ambient oxygen concentration as of the time of cell culture is significantly lower than that in the atmosphere. Specifically, conditions involving lower oxygen concentrations than the ambient oxygen concentrations in the 5-10% $CO_2$/95-90% air atmosphere, which is commonly used for ordinary cell culture, can be mentioned; examples include conditions involving an ambient oxygen concentration of 18% or less. Preferably, the ambient oxygen concentration is 15% or less (e.g., 14% or less, 13% or less, 12% or less, 11% or less and the like), 10% or less (e.g., 9% or less, 8% or less, 7% or less, 6% or less and the like), or 5% or less (e.g., 4% or less, 3% or less, 2% or less and the like). The ambient oxygen concentration is preferably 0.1% or more (e.g., 0.2% or more, 0.3% or more, 0.4% or more and the like), 0.5% or more (e.g., 0.6% or more, 0.7% or more, 0.8% or more, 0.95% or more and the like), or 1% or more (e.g., 1.1% or more, 1.2% or more, 1.3% or more, 1.4% or more and the like).

Although any method of creating a hypoxic state in a cellular environment can be used, the easiest way is to culture cells in a $CO_2$ incubator permitting adjustments of oxygen concentration, and this represents a suitable case. $CO_2$ incubators permitting adjustment of oxygen concentration are commercially available from various manufacturers (e.g., $CO_2$ incubators for hypoxic culture manufactured by Thermo scientific, Ikemoto Scientific Technology, Juji Field, Wakenyaku etc.).

The time of starting cell culture under hypoxic conditions is not particularly limited, as far as iPS cell establishment efficiency is not prevented from being improved compared with the normal oxygen concentration (20%). Although the culture may be started before the somatic cell is contacted with the nuclear reprogramming substance and the inhibitor of p38 function, or at the same time as the contact, or after the contact, it is preferable, for example, that the culture under hypoxic conditions be started just after the somatic cell is contacted with the nuclear reprogramming substance and the inhibitor of p38 function, or at a given time interval after the contact [e.g., 1 to 10 (e.g., 2, 3, 4, 5, 6, 7, 8 or 9) days].

The duration of cultivation of cells under hypoxic conditions is not particularly limited, as far as iPS cell establishment efficiency is not prevented from being improved compared with the normal oxygen concentration (20%); examples include, but are not limited to, periods of 3 days or more, 5 days or more, 7 days or more or 10 days or more, and 50 days or less, 40 days or less, 35 days or less or 30 days or less and the like. Preferred duration of cultivation under hypoxic conditions varies depending on ambient oxygen concentration; those skilled in the art can adjust as appropriate the duration of cultivation according to the oxygen concentration used. In an embodiment of the present invention, if iPS cell candidate colonies are selected with drug resistance as an index, it is preferable that a normal oxygen concentration be restored from hypoxic conditions before starting drug selection.

Furthermore, preferred starting time and preferred duration of cultivation for cell culture under hypoxic conditions also vary depending on the choice of nuclear reprogramming substance used, iPS cell establishment efficiency at normal oxygen concentrations and the like.

After the nuclear reprogramming substance and inhibitor of p38 function are brought into contact, the cell can be cultured under conditions suitable for cultivation of, for example, ES cells. In the case of mouse cells, the culture be carried out with the addition of Leukemia Inhibitory Factor (LIF) as a differentiation suppression factor to an ordinary medium. Meanwhile, in the case of human cells, it is desirable that basic fibroblast growth factor (bFGF) and/or stem cell factor (SCF) be added in place of LIF. Usually, the cell is cultured in the co-presence of mouse embryonic fibroblasts (MEFs) treated with radiation or an antibiotic to terminate the cell division, as feeder cells. As the MEF, usually STO cells and the like are commonly used, but for inducing iPS cells, SNL cells (McMahon, A. P. & Bradley, A. Cell 62, 1073-1085 (1990)) and the like are commonly used. Co-culture with feeder cells may be started before contact of the nuclear reprogramming substance and the inhibitor of p38 function, at the time of the contact, or after the contact (for example, 1-10 days later).

A candidate colony of iPS cells can be selected by a method with drug resistance and reporter activity as indicators, and also by a method based on macroscopic examination of morphology. As an example of the former, a colony positive for drug resistance and/or reporter activity is selected using a recombinant cell wherein a drug resistance gene and/or a reporter gene is targeted to the locus of a gene highly expressed specifically in pluripotent cells (for example, Fbx15, Nanog, Oct3/4 and the like, preferably Nanog or Oct3/4). As examples of such recombinant cells, a MEF derived from a mouse wherein the βgeo (which encodes a fusion protein of β-galactosidase and neomycin phosphotransferase) gene is knocked-in to the Fbx15 gene locus (Takahashi & Yamanaka, Cell, 126, 663-676 (2006)), or a MEF derived from a transgenic mouse wherein the green fluorescent protein (GFP) gene and the puromycin resistance gene are integrated in the Nanog gene locus (Okita et al., Nature, 448, 313-317 (2007)) and the like can be mentioned. Meanwhile, methods of macroscopic examination of morphology include, for example, the method described by Takahashi et al. in Cell, 131, 861-872 (2007). Although methods using reporter cells are convenient and efficient, colony selection by macroscopic examination is desirable from the viewpoint of safety when iPS cells are prepared for the purpose of human treatment.

The identity of the cells of the selected colony as IFS cells can be confirmed by positive responses to Nanog (or Oct3/4) reporters (puromycin resistance, GFP positivity and the like), as well as by the formation of a visible ES cell-like colony, as described above; however, to increase the accuracy, it is possible to perform tests such as alkaline phosphatase staining, analyzing the expression of various ES-cell-specific genes, and transplanting the cells selected to a mouse and confirming teratoma formation.

The iPS cells thus established can be used for various purposes. For example, by utilizing a method of differentiation induction reported with respect to ES cells, differentiation into various cells (e.g., myocardial cells, blood cells, nerve cells, vascular endothelial cells, insulin-secreting cells and the like) from iPS cells can be induced. Therefore, inducing iPS cells using a somatic cell collected from a patient or another person with the same or substantially the same HLA type as that of the patient would enable stem cell therapy by autogeneic transplantation, wherein the iPS cells are differentiated into desired cells (that is, cells of an affected organ of the patient, cells that have a therapeutic effect on disease, and the like), which are transplanted to the patient. Furthermore, because functional cells (e.g., hepatocytes) differentiated from iPS cells are thought to better reflect the actual state of the functional cells in vivo than do corresponding existing cell lines, they can also be suitably used for in vitro screening for the effectiveness and toxicity of pharmaceutical candidate compounds and the like.

The present invention is hereinafter described in further detail by means of the following examples, to which, however, the invention is never limited.

EXAMPLES

Example 1

Investigation with p38 Inhibitors

The effects of various p38 inhibitors on the efficiency of iPS cell establishment were examined.
1) Comparison of effects of p38 inhibitors on mouse iPS cell colonies (4 genes introduced)

Mouse embryonic fibroblasts (MEFs) from a Nanog reporter mouse carrying Nanog-GFP—IRES-Puro$^r$ [Okita K. et al, Nature 448, 313-317 (2007)] were transfected with four genes using a retrovirus to induce iPS cells.

Each retrovirus for reprogramming was prepared by transferring each of retroviral expression vectors (pMXs-Oct3/4, pMXs-Sox2, pMXs-Klf4, pMXs-cMyc:Cell, 126, 663-676 (2006)) to Plat-E cells (Morita, S. et al., Gene Ther. 7, 1063-1066) that had been seeded to a 6-well culture plate (Falcon) at $0.6 \times 10^6$ cells per well on the day before. The cells were cultured at 37° C. in the presence of 5% $CO_2$ using DMEM/10% FCS [a culture broth prepared by adding 10% fetal calf serum to DMEM (Nacalai Tesque)]. To facilitate vector transfer, 4.5 μL of FuGene6 transfection reagent (Roche) was placed in 100 μL of Opti-MEM I Reduced-Serum Medium (Invitrogen), and the medium was allowed to stand at room temperature for 5 minutes. Subsequently, 1.5 μg of each expression vector was added, and the medium was allowed to further stand at room temperature for 15 minutes, after which they were added to the Plat-E culture broth. On day 2, the Plat-E supernatant was replaced with a fresh supply of the medium. On day 3, the culture supernatant was recovered and filtered through a 0.45 μm sterile filter (Whatman), and polybrene (Nacalai) was added at 4 μg/mL to yield a viral liquid.

Mouse embryonic fibroblasts (MEFs) were isolated from a fetal Nanog reporter mouse (13.5 days after fertilization). Not expressing the Nanog gene, MEFs do not express EGFP and do not emit green fluorescence. Not expressing the puromycin resistance gene as well, MEFs are susceptible to the antibiotic puromycin. As such, MEFs were seeded to a 6-well culture plate (Falcon), previously coated with 0.1% gelatin (Sigma), at $1.0 \times 10^5$ cells per well. DMEM/10% FCS served as the culture broth at 37° C. in the presence of 5% $CO_2$. The following day, each retrovirus liquid was added, and this was followed by overnight infection to introduce the genes.

On day 1 after the viral infection, the medium for the MEFs was removed, and the cells were washed by the addition of 1 mL of PBS. After removing the PBS, 0.25% Trypsin/1 mM EDTA (Invitrogen) was added, and a reaction was carried out at 37° C. for about 5 minutes. After the cells floated up, the cells were suspended by the addition of an ES cell culture medium and 2500 cells were seeded to a 100 mm dish having mitomycin C-treated STO feeder cells seeded thereto previously. Cultivation was continued while replacing the ES cell culture medium with a fresh supply of the same medium every two days until a visible colony emerged.

To determine the effects of p38 inhibitors on the establishment of iPS cells by the introduction of the four mouse genes, cultivation was continued with the addition of 10 μM of the p38 inhibitor 5B202190, SB239063, or SB203580

(Calbiochem Company) to the medium per the schedule shown below. All these inhibitors were used in solution in DMSO.
1. Oct3/4, Sox2, Klf4, c-Myc, each derived from mouse, saline
2. Oct3/4, Sox2, Klf4, c-Myc, each derived from mouse, DMSO
3. Oct3/4, Sox2, Klf4, c-Myc, each derived from mouse, SB202190 10 µM Day 1-4)
4. Oct3/4, Sox2, Klf4, c-Myc, each derived from mouse, SB202190 10 µM (Day 1-8)
5. Oct3/4, Sox2, Klf4, c-Myc, each derived from mouse, SB202190 10 µM (Day 9-16)
6. Oct3/4, Sox2, Klf4, c-Myc, each derived from mouse, SB202190 10 µM (Day 1-16)
7. Oct3/4, Sox2, Klf4, c-Myc, each derived from mouse, SB239063 10 µM (Day 1-4)
8. Oct3/4, Sox2, Klf4, c-Myc, each derived from mouse, SB239063 10 µM (Day 1-8)
9. Oct3/4, Sox2, Klf4, c-Myc, each derived from mouse, SB239063 10 µM (Day 9-16)
10. Oct3/4, Sox2, Klf4, c-Myc, each derived from mouse, SB239063 10 µM (Day 1-16)
11. Oct3/4, Sox2, Klf4, c-Myc, each derived from mouse, SB203580 10 µM (Day 1-4)
12. Oct3/4, Sox2, Klf4, c-Myc, each derived from mouse, SB203580 10 µM (Day 1-8)
13. Oct3/4, Sox2, Klf4, c-Myc, each derived from mouse, SB203580 10 µM (Day 9-16)
14. Oct3/4, Sox2, Klf4, c-Myc, each derived from mouse, SB203580 10 µM (Day 1-16)

On day 14 after the infection, selection was started using puromycin (1.5 µg/mL). Visible colonies began to emerge around day 8 and became GFP-positive. On days 21 and 28 after the infection, GFP-positive colonies were counted. The results in comparison with control groups treated with physiological saline or DMSO are shown in FIG. 1.

When the cells were treated with SB239063 or SB203580 early on days 1 to 4 after the infection, the colony count tended to increase compared with the cells treated with physiological saline or DMSO, the effect being remarkable when measured on day 28 after the infection. Nanog-GFP-positive colonies were counted. When SB202190 or SB239063 was added in early on days 1 to 4 after the infection, the number of positive colonies increased compared with the cells treated with physiological saline or DMSO. These results demonstrate that the efficiency of iPS cell establishment rises as a result of functional inhibition of p38.

2) Comparison of Effects of p38 Inhibitors on Mouse iPS Cell Colonies (3 Genes Introduced)

Figure 2:
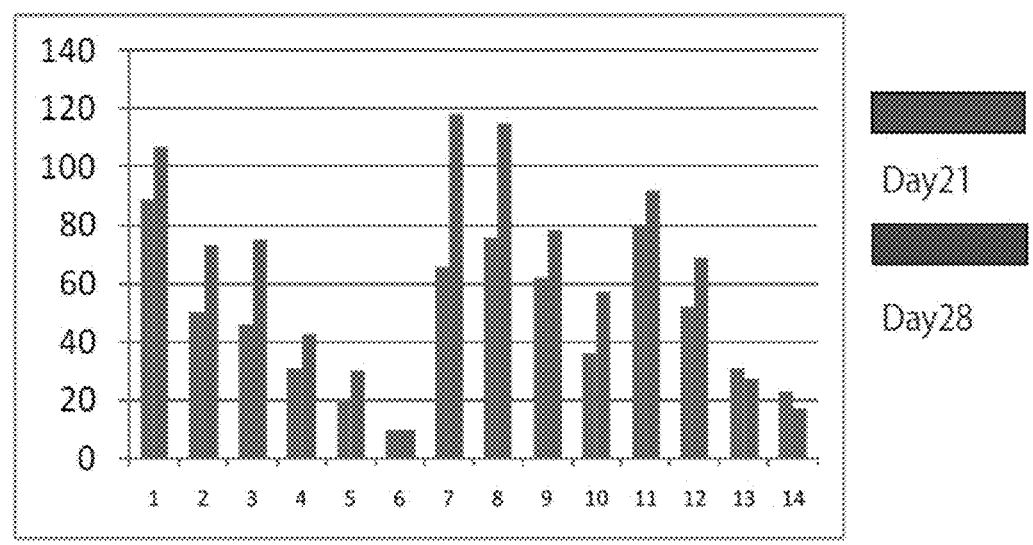
FIG. 2 is a graphic representation showing the colony counts obtained on day 21 (left bar) or 28 (right bar) after infection by introducing three genes (Oct3/4, Klf4, Sox2) into mouse dermal fibroblasts (MEFs), and culturing the cells in the presence of various p38 inhibitors. The upper panel shows total colony counts; the lower panel shows Nanog GFP-positive colony counts. The vertical axis indicates the number of iPS cell colonies found on a 10 cm dish.
Figure 2:
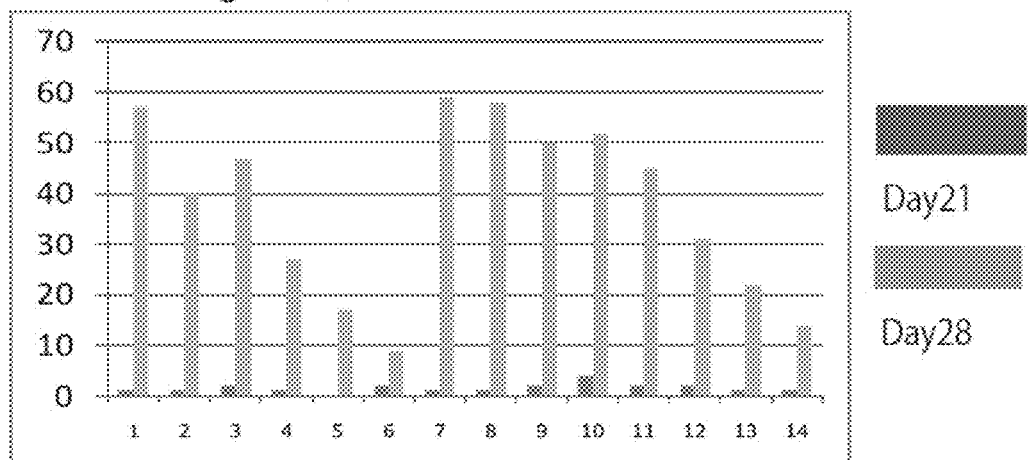

Three genes were introduced using a retrovirus by the same experimental procedures as the above. The cells were cultured at a cell density of $2\times10^4$ cells/10 cm dish, with the addition of 10 µM of SB202190, SB239063, or SB203580 (Calbiochem Company) to the medium per the schedule shown below, and the establishment efficiency was compared.
1. Oct3/4, Sox2, Klf4, each derived from mouse, saline
2. Oct3/4, Sox2, Klf4, each derived from mouse, DMSO
3. Oct3/4, Sox2, Klf4, each derived from mouse, SB202190 10 µM (Day 1-4)
4. Oct3/4, Sox2, Klf4, each derived from mouse, SB202190 10 µM (Day 1-8)
5. Oct3/4, Sox2, Klf4, each derived from mouse, SB202190 10 µM (Day 9-16)
6. Oct3/4, Sox2, Klf4, each derived from mouse, SB202190 10 µM (Day 1-16)
7. Oct3/4, Sox2, Klf4, each derived from mouse, SB239063 10 µM (Day 1-4)
8. Oct3/4, Sox2, Klf4, each derived from mouse, SB239063 10 µM (Day 1-8)
9. Oct3/4, Sox2, Klf4, each derived from mouse, SB239063 10 µM (Day 9-16)
10. Oct3/4, Sox2, Klf4, each derived from mouse, SB239063 10 µM (Day 1-16)
11. Oct3/4, Sox2, Klf4, each derived from mouse, SB203580 10 µM (Day 1-4)
12. Oct3/4, Sox2, Klf4, each derived from mouse, SB203580 10 µM (Day 1-8)
13. Oct3/4, Sox2, Klf4, each derived from mouse, SB203580 10 µM (Day 9-16)
14. Oct3/4, Sox2, Klf4, each derived from mouse, SB203580 10 µM (Day 1-16), The results are shown in FIG. 2. The total number of to colonies and the number of Nanog-GFP-positive colonies increased when the cells were treated with SB239063, compared with the cells treated with physiological saline or DMSO. When SB203580 was added in the initial stage after the infection, the number of positive cells increased compared with DMSO treatment.

These results demonstrate that in the case of the introduction of three genes as well, the efficiency of iPS cell establishment rises as a result of functional inhibition of p38.

3) Comparison of Effects of p38 Inhibitors on Human iPS Cell Colonies (4 Genes Introduced)

Human dermal fibroblasts (HDF 1616 line) were treated using a lentivirus (pLenti6/UbC-Slc7a1) according to the method described by Takahashi, K. et al. in Cell, 131: 861-872 (2007), to express the mouse ecotropic virus receptor Slc7a1 gene. These cells were seeded to a 6-well culture plate (Falcon), previously coated with 0.1% gelatin (Sigma), at $1.0\times10^5$ cells per well. The following day, the four human genes were introduced using a retrovirus according to the method described by Takahashi, K. et al. in Cell, 131: 861-872 (2007). On day 4 after the infection, $2.0\times10^5$ cells were seeded to a 100 mm dish, containing previously seeded feeder cells. To determine the effect of a p38 inhibitor, SB202190 was added simultaneously with the infection (Day 0), or on day 5 after the infection, and the efficiency of iPS cell establishment was compared.

Figure 3:
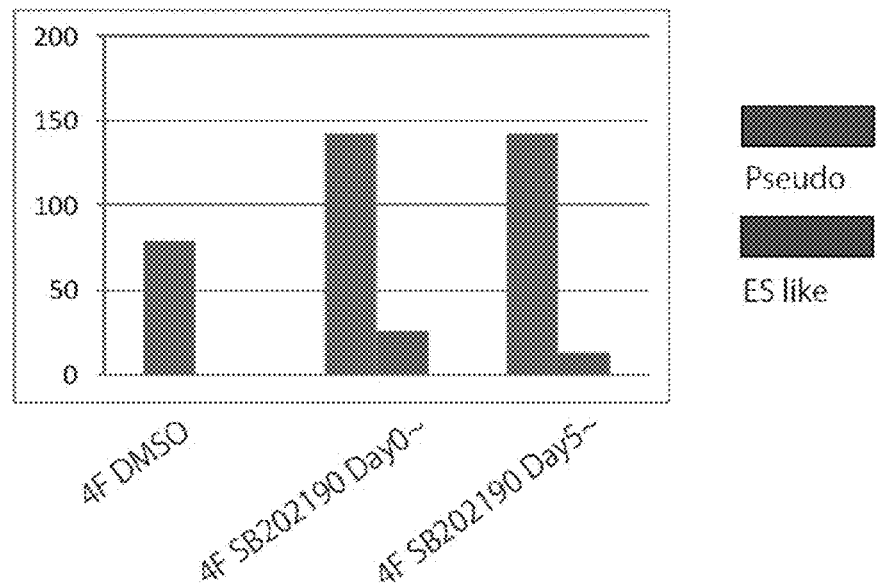
FIG. 3 is a graphic representation showing the human iPS cell colony counts obtained on day 16 after infection by introducing four genes (Oct3/4, Klf4, Sox2, C-myc) into human dermal fibroblasts (HDF 1616), and adding SB202190 on day 0 or 5 after infection. The upper panel shows the results obtained by seeding the cells at a cell density of $200 \times 10^3$ cells/10 cm dish; the lower panel shows the results obtained at a cell density of $30 \times 10^3$ cells/10 cm dish. The vertical axis indicates the number of iPS cell colonies found on the 10 cm dish. In this figure, "Psuedo" (left bar) stands for non-iPS cells, and "ES like" (right bar) for iPS cells.
Figure 3:
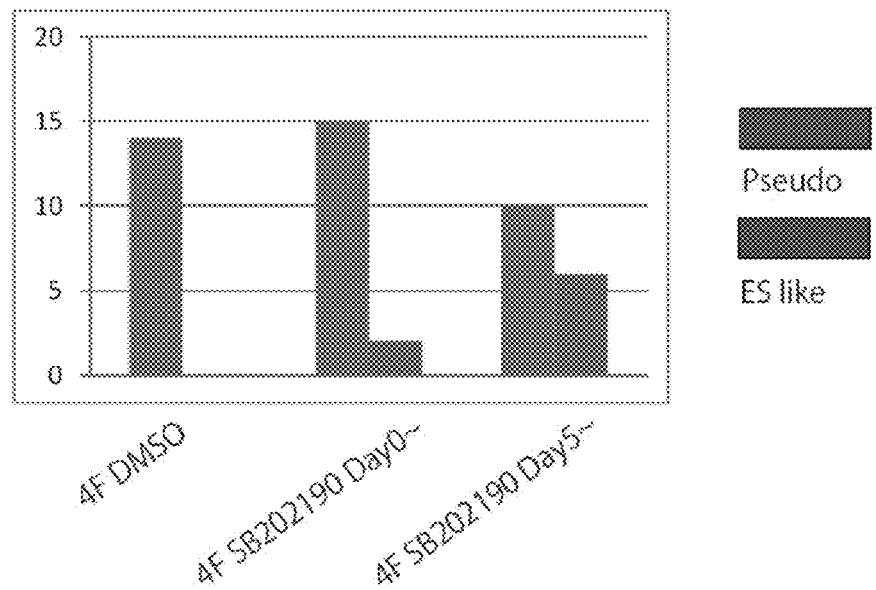

On day 16 after the infection, iPS cell colonies were counted. The results are shown in the upper panel in FIG. 3. In the context of introduction of the four genes (Oct3/4, Sox2, Klf4, C-Myc), the number of human iPS cell colonies increased with the addition of SB202190 in the initial stage after the infection, compared with the addition of DMSO for control and the addition of SB202190 on day 5 after the infection.

The four genes were introduced using a retrovirus in the same manner, but at a different cell density ($3\times10^4$ cells/10 cm dish), with simultaneous addition of SB202190 (Day 0). SB202190 was added also on day 5 after the infection, and the efficiency of iPS cell establishment was compared.

On day 16 after the infection, colony sizes were measured. The results are shown in the lower panel in FIG. 3. Even when the cell density was changed, the number of iPS cell colonies increased with the addition of SB202190 along with the four factors (Oct3/4, Sox2, Klf4, C-Myc), compared with the addition of DMSO. It was also found that at the lower cell density, the efficiency of iPS cell establishment was higher when SB202190 was added on day 5 after the infection than when added simultaneously with the infection.

Hence, it was found that p38 inhibitors promote colony growth and are highly effective in increasing the efficiency of iPS cell establishment.

4) Comparison of Effects of Various p38 Inhibitors on Human iPS Cell Colonies (4 Genes Introduced, 3 Genes Introduced)

Human dermal fibroblasts (Tig109 line) were treated using a lentivirus (pLenti6/UbC-Slc7a1) according to the method described by Takahashi, K. et al. in Cell, 131: 861-872 (2007), to express the mouse ecotropic virus receptor Slc7a1 gene. These cells ($2\times10^5$ cells/10 cm dish) were transfected with the four genes using a retrovirus according to the method described by Takahashi, K. et al. in Cell, 131: 861-872 (2007); each compound was added per the schedule shown below.

1. Oct3/4, Sox2, Klf4, c-Myc, each derived from human, saline
2. Oct3/4, Sox2, Klf4, c-Myc, each derived from human, DMSO (Day 5-35)
3. Oct3/4, Sox2, Klf4, c-Myc, each derived from human, SB202190 10 µM (Day 5-20)
4. Oct3/4, Sox2, Klf4, c-Myc, each derived from human, SB239063 10 µM (Day 5-20)
5. Oct3/4, Sox2, Klf4, c-Myc, each derived from human, SB202190 10 µM (Day 21-35)
6. Oct3/4, Sox2, Klf4, c-Myc, each derived from human, SB239063 10 µM (Day 21-35)
7. Oct3/4, Sox2, Klf4, c-Myc, each derived from human, SB202190 10 µM (Day 5-35)
8. Oct3/4, Sox2, Klf4, c-Myc, each derived from human, SB239063 10 µM (Day 5-35)

Figure 4:
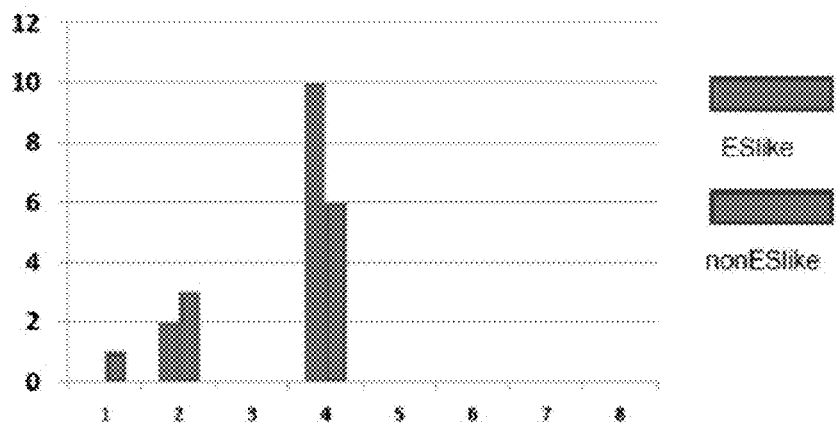
FIG. 4 is a graphic representation showing the human iPS cell colony counts obtained by introducing four genes (Oct3/4, Klf4, Sox2, C-myc) into human dermal fibroblasts (Tig109), and culturing the cells in the presence of various p38 inhibitors. Panels A, B and C show the results obtained on days 24, 32 and 40 after infection, respectively. The vertical axis indicates the number of iPS cell colonies found on the 10 cm dish. In this figure, "non ES like" (right bar) stands for non-iPS cells, and "ES like" (left bar) for iPS cells.
Figure 4:
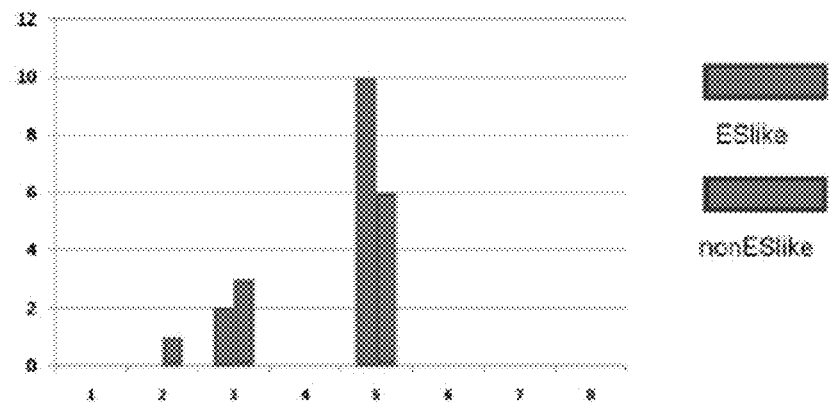
Figure 4:
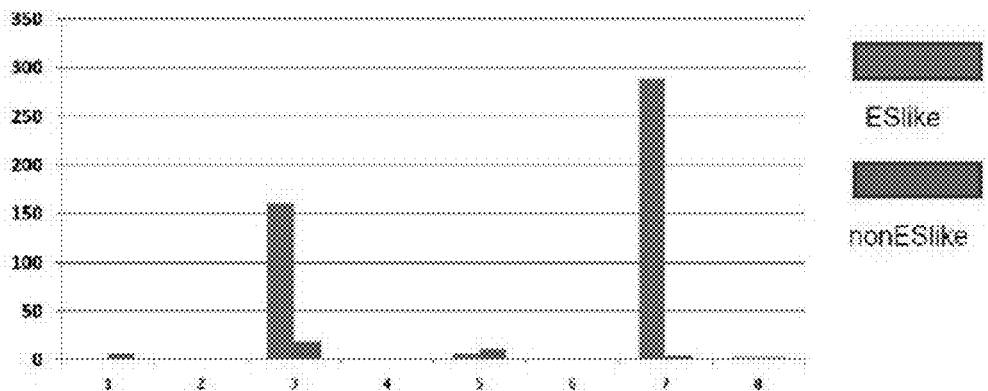

On days 24, 32, and 40 after the infection, iPS cell colonies were counted. The results are shown in FIG. 4. When the four factors (Oct3/4, Sox2, Klf4, C-Myc) were combined with SB239063 added on days 5 to 20 after the infection, the number of human iPS cell colonies increased on day 24 after the infection. On day 32 after the infection, the cells cultured with the addition of SB202190 were found to be capable of increasing the number of iPS cell colonies, with remarkable effects observed in the cells cultured with the addition of the inhibitor on day 21 (before the observation) to day 35 after the infection. On day 40 after the infection, no iPS cell colonies were observed in either control group, whereas two IFS cell colonies emerged with the addition of SB239063, and the number of iPS colonies increased remarkably with the addition of SB202190.

Subsequently, three genes (Oct3/4, Sox2, Klf4) were introduced using a retrovirus in the same manner, and the efficiency of iPS cell establishment was compared.

1. Oct3/4, Sox2, Klf4, each derived from human, saline
2. Oct3/4, Sox2, Klf4, each derived from human, DMSO (Day 5-35)
3. Oct3/4, Sox2, Klf4, each derived from human, SB202190 10 µM (Day 5-20)
4. Oct3/4, Sox2, Klf4, each derived from human, SB239063 10 µM (Day 5-20)
5. Oct3/4, Sox2, Klf4, each derived from human, SB202190 10 µM to (Day 21-35)
6. Oct3/4, Sox2, Klf4, each derived from human, SB239063 10 µM (Day 21-35)
7. Oct3/4, Sox2, Klf4, each derived from human, SB202190 10 µM (Day 5-35)
8. Oct3/4, Sox2, Klf4, each derived from human, SB239063 10 µM (Day 5-35)

Figure 5:
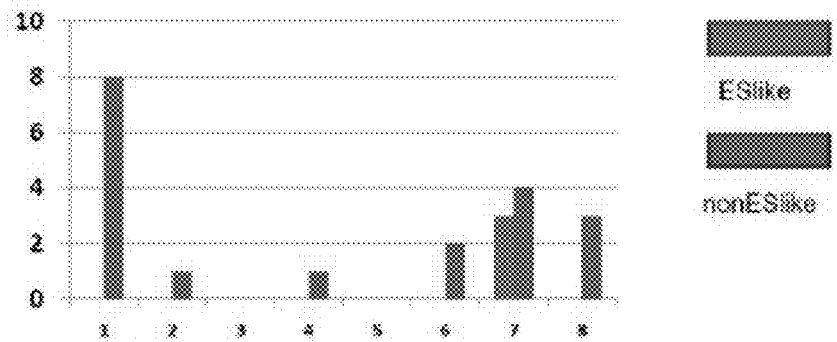
FIG. 5 is a graphic representation showing the human iPS cell colony counts obtained by introducing three genes (Oct3/4, Klf4, Sox2) into human dermal fibroblasts (Tig109), and culturing the cells in the presence of various p38 inhibitors. Panels A and B show the results obtained on days 32 and 40 after infection, respectively. The vertical axis indicates the number of iPS cell colonies found on the 10 cm dish. In this figure, "non ES like" (right bar) stands for non-iPS cells, and "ES like" (left bar) for iPS cells.
Figure 5:
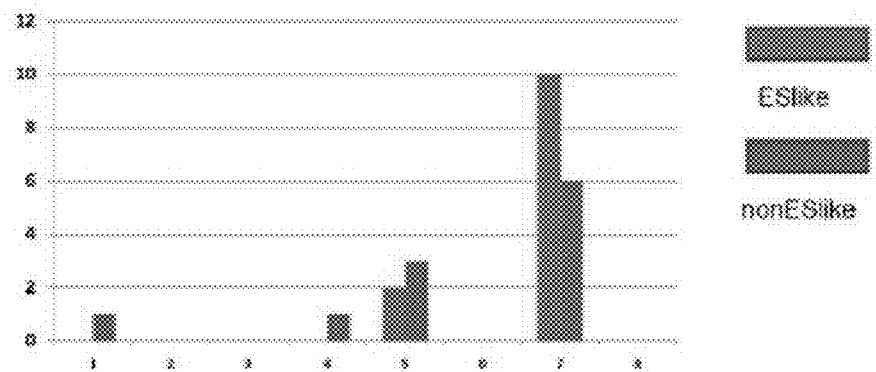

The results are shown in FIG. 5. As observed on day 32 after the infection, the number of positive colonies increased with the addition of SB202190, compared with physiological saline and DMSO for control. On day 40 after the infection, the number of iPS cell colonies increased remarkably with the addition of SB202190, compared with physiological saline and DMSO for control.

Hence, it was found that p38 inhibitors are effective in improving the efficiency of iPS cell establishment by increasing the number of colonies.

The contents disclosed in any publication cited herein, including patents and patent applications, are hereby incorporated in their entireties by reference, to the extent that they have been disclosed herein.

This application is based on U.S. provisional patent application No. 61/382,707, the contents of which are hereby incorporated by reference.

The invention claimed is:

1. A method of improving the efficiency of establishment of induced pluripotent stem cells, consisting essentially of a step of introducing into a somatic cell into which a nuclear reprogramming substance is simultaneously introduced or has been previously introduced within the past 5 days
   (i) a chemical inhibitor of p38, (ii) a dominant negative mutant of p38 or a DNA that encodes the same, or (iii) a nucleic acid selected from the group consisting of p38 siRNAs, p38 shRNAs and DNAs that encode the same, thereby improving the efficiency of establishment of induced pluripotent stem cells.

2. The method according to claim 1, wherein a chemical inhibitor of p38 is introduced into the somatic cell.

3. The method according to claim 2, wherein the chemical inhibitor of p38 is at least one substance selected from the group consisting of SB202190 and SB239063.

4. The method according to claim 1, wherein a dominant negative mutant of p38 or a DNA that encodes the same is introduced into the somatic cell.

5. The method according to claim 1, wherein a nucleic acid selected from the group consisting of p38 siRNAs, p38 shRNAs and DNAs that encode the same is introduced into the somatic cell.

6. A method of producing induced pluripotent stem cells, consisting essentially of the following steps:
   introducing a nuclear reprogramming substance into a somatic cell, and
   introducing into the somatic cell a p38 inhibitor selected from (i) a chemical inhibitor of p38, (ii) a dominant negative mutant of p38 or a DNA that encodes the same, and (iii) a nucleic acid selected from the group consisting of p38 siRNAs, p38 shRNAs, and DNAs that encode the same, wherein introducing the p38 inhibitor occurs simultaneously with, or within 5 days of, introducing the nuclear reprogramming substance, thereby producing induced pluripotent stem cells.

7. The method according to claim 6, wherein the p38 inhibitor is a chemical inhibitor of p38.

8. The method according to claim 7, wherein the chemical inhibitor of p38 is at least one substance selected from the group consisting of SB202190 and SB239063.

9. The method according to claim 6, wherein the p38 inhibitor is a dominant negative mutant of p38 or a DNA that encodes the same.

10. The method according to claim 6, wherein the p38 inhibitor is a nucleic acid selected from the group consisting of p38 siRNAs, p38 shRNAs, and DNAs that encode the same.

11. The method according to claim 6, wherein the nuclear reprogramming substances are Oct3/4, Klf4 and Sox2, or nucleic acids that encode the same.

12. The method according to claim 6, wherein the nuclear reprogramming substances are Oct3/4, Klf4, Sox2 and at least one selected from the group consisting of (a) c-Myc or L-Myc, (b) Nanog, (c) Lin28 or Lin28B, and (d) Glis1, or nucleic acids that encode the same.

13. The method according to claim 1, wherein the induced pluripotent stem cell is a human cell.

14. The method according to claim 2, wherein the induced pluripotent stem cell is a human cell.

15. The method according to claim 14, wherein the chemical inhibitor of p38 is SB202190.

16. The method according to claim 6, wherein the induced pluripotent stem cell is a human cell.

17. The method according to claim 7, wherein the induced pluripotent stem cell is a human cell.

18. The method according to claim 17, wherein the chemical inhibitor of p38 is SB202190.

* * * * *

SEQUENCE LISTING

```
<160> NUMBER OF SEQ ID NOS: 4

<210> SEQ ID NO 1
<211> LENGTH: 3560
<212> TYPE: DNA
<213> ORGANISM: Mus musculus

<400> SEQUENCE: 1
gatctggatt cagagcgggg cctccttgga gctgttctcg cgagagttcc gcgagaggct      60
cccggccgct gcctgtggga tcgccgccac tggagcccaa gcggggcgct gaagcgcgag     120
cgggtgtctt gcgcgtcgg cgtgcgctcc ctccccgggg agcggctgca ggaggaccgc      180
ggcgggagca gcctcgagcc gtgcagccgg ctccggcacc ttgccgacgc tcgtaggagc     240
cgccgcggct gacaggggcg gcgggtcgca gcctccacac ctgcgcgggt ggcgggcgcg     300
gggtccggtc tgccgcgggc gggcgcagag gagagcgtgc ggctgcaggc aggagccccc     360
gctcggccac ctcctcgccc cgctgctgcc gctggaagat gtcgcaggag aggcccacgt     420
tctaccggca ggagctgaac aagaccatct gggaggtgcc cgaacgatac cagaacctgt     480
```

-continued

| | |
|---|---|
| ccccggtggg ctcgggcgcc tatggctcgg tgtgtgctgc ttttgataca aagacggggc | 540 |
| atcgtgtggc agttaagaag ctgtcgagac cgtttcagtc catcattcac gccaaaagga | 600 |
| cctaccgaga gttgcgtctg ctgaagcaca tgaaacacga aaatgtgatt ggtctgttgg | 660 |
| atgtgttcac acccgcaagg tcactggagg aattcaatga cgtgtacctg gtgacccatc | 720 |
| tcatggggc ggacctgaac aacatcgtga agtgccagaa gctgaccgac gaccacgttc | 780 |
| agtttctcat ctaccagatc ctccgagggc tgaagtatat acattcggct gacataattc | 840 |
| acagggacct aaagcccagc aacctagctg tgaacgaaga ctgtgagctc aagattctgg | 900 |
| attttgggct ggctcggcac actgatgatg agatgacagg ctacgtggct accaggtggt | 960 |
| accgagcccc agagatcatg ctgaattgga tgcactataa ccagacagtg gatatttggt | 1020 |
| ccgtgggctg catcatggct gagctgttga ccggaagaac gttgtttcct ggtacagacc | 1080 |
| atattgatca gttgaagctc attttaagac tcgttggaac cccaggggct gagcttctga | 1140 |
| agaaaatctc ctcagagtct gcaagaaact acattcagtc tctggcccag atgccgaaga | 1200 |
| tgaacttcgc aaatgtattt attggtgcca atccctggc tgtcgaccta ctggagaaga | 1260 |
| tgctcgtttt ggactcagat aagaggatca cagcagccca agctcttgcg catgcctact | 1320 |
| ttgctcagta ccacgaccct gatgatgagc ctgttgctga cccttatgac cagtcctttg | 1380 |
| aaagcaggga ccttctcata gatgagtgga agagcctgac ctatgatgaa gtcatcagct | 1440 |
| ttgtgccacc accccttgac caagaagaaa tggagtcctg agcacctggt ttctgttctg | 1500 |
| tctatctcac ttcactgtga ggggaagacc ttctcatggg aactctccaa ataccattca | 1560 |
| agtgcctctt gttgaaagat tccttcatgg tggaagggg tgcatgtatg tgttagtgtt | 1620 |
| tgtgtgtgtg tgtgtgtctg tctgttcgtc tgtccaccta tctttgtgga agtcactgtg | 1680 |
| atggtagtga ctttatgagt tgtgaatggt ccttggcagt ctgcctgctt tctcagagtc | 1740 |
| tgggcaggcc gatgggaact gtcatctcct tagggatgtg tgtgttcagt gcaaagtaag | 1800 |
| aaatatgaaa atatccctgt tcttagttac cttgccactt tggcttctcc tgtgccctg | 1860 |
| cctttaccat atcagtgaca gagagaggct gcttcaggtc tgaggctatc cctcagccat | 1920 |
| gcataaagtc caagagaacc aactggctcc tggtctctag cctgtgaccg gcttgcttaa | 1980 |
| tgtcctcaga acctgacagg tatgttcaaa actgtcagtc tgtttgtgcc ttaaaagggt | 2040 |
| gagaagggcg cgtagatagt tacagagtct cagctgctga cgttctgagc caggcaagtg | 2100 |
| cacggggctg ttggatggcc agtggggagc tggaaaaaac aaggcagcct ttaggaaggc | 2160 |
| catggtgcat gtgtgtgcat gcgtgtatgt gcagccgccc tccctcactt caggagcaag | 2220 |
| ctgtttgctg tgcttaccct tcacctcagt gcagaggtct ccagtgccga gcacaggcac | 2280 |
| ctgccatcag tagttcctgt gtcatcttca catctagcag agcacggatg tgtttgcatg | 2340 |
| ctgtgctctt ggagcttgtc ctgtcttctg gaagccctgg acaaggcgtg tgaaggcttc | 2400 |
| ccagaagttc ctgtccacat tgcctccgcc caccgacgcc atgggcacac tgctccctcc | 2460 |
| tcctcctcca gctactttgt gttgaacaca attgattctc caggtgctca tggtgcagga | 2520 |
| aaacaggaca gacagagagc acctgaaccc ttgccatctg atgtcaccaa ttcaggaaaa | 2580 |
| cgagtcctct cctaggacta tccccggttc tggaaatcat gttctcctca ctcatggtga | 2640 |
| caagctaaga aagctgaaca aagggagaga cgagagcgcc tgaagccagg agctccttta | 2700 |
| ctatctttct caaagggtt gttagacaca aaccaagtca tcaaggcccc gctcctctcc | 2760 |
| tcggaagggt cccccacccc ccggcagctt gacactgaat ccagtgtcaa tttggggaga | 2820 |
| aagcagtttt gtcttggaat tttgtatgtt gtaggaatcc ttagagagtg tggttccttc | 2880 |

```
tgatggggag aaagggcaaa ttattttaat attttgtatt ttcacccttta taaacatgaa    2940 tcctcagggg tgaagaactg tttgcataat tttctgaatt ttgagcactt tgtgctatat    3000
aaggacccat atttaagctt tgtgtgcagt aagaaagtgt aaagccaatt ccagtgttgg    3060
acgtgacagg tcttgtgttt aggtcaaggt gtctcctctc agtgcaggga catgcctgct    3120
ctgtggggca ggcgaggacc ctgaatcatt tggagcccag aaggaggcag actggccagg    3180
tctcaccacc tcagtgtgca gttcaactcc atgccatccc atcaagatgg ttagtagca    3240 gtgtctgttt ttgaatgcca agtgtgattt ccaacaattc tgctctggtt atttcattga    3300
agacatcttt gcacatgtga ccatgctgtg ttaggggctg tgttccaggg actggactcg    3360
aagctagaac tggcagaaga gttctggcat ccacagcgca atgctgccac cacccagttt    3420
cttcatcaga agacaaggga acgagaaaac tgctgttcgt ttgtatttgt gaacttggct    3480
gtaatctggt atgccatagg atgtcagata ataccactgg ttaaaataaa gcctagtttt    3540
caaattcaaa aaaaaaaaaa                                                3560
```

```
<210> SEQ ID NO 2
<211> LENGTH: 4353
<212> TYPE: DNA
<213> ORGANISM: Homo sapiens

<400> SEQUENCE: 2
```

```
ttctctcacg aagccccgcc cgcggagagg ttccatattg ggtaaaatct cggctctcgg      60
agagtcccgg gagctgttct cgcgagagta ctgcgggagg ctcccgtttg ctggctcttg     120
gaaccgcgac cactggagcc ttagcgggcg cagcagctgg aacgggagta ctgcgacgca     180
gcccggagtc ggccttgtag gggcgaaggt gcagggagat cgcggcgggc gcagtcttga     240
gcgccggagc gcgtccctgc ccttagcggg gcttgcccca gtcgcagggg cacatccagc     300
cgctgcggct gacagcagcc gcgcgcgcgg gagtctgcgg ggtcgcggca gccgcacctg     360
cgcgggcgac cagcgcaagg tccccgcccg gctgggcggg cagcaagggc cggggagagg     420
gtgcgggtgc aggcggggc cccacagggc caccttcttg cccggcgct gccgctggaa     480 aatgtctcag gagaggccca cgttctaccg gcaggagctg aacaagacaa tctgggaggt     540
gcccgagcgt taccagaacc tgtctccagt gggctctggc gcctatggct ctgtgtgtgc     600
tgcttttgac acaaaacgg ggttacgtgt ggcagtgaag aagctctcca gaccatttca     660
gtccatcatt catgcgaaaa gaacctacag agaactgcgg ttacttaaac atatgaaaca     720
tgaaaatgtg attggtctgt ggacgttttt tacacctgca aggtctctgg aggaattcaa     780
tgatgtgtat ctggtgaccc atctcatggg ggcagatctg aacaacattg tgaaatgtca     840
gaagcttaca gatgaccatg ttcagttcct tatctaccaa attctccgag gtctaaagta     900
tatacattca gctgacataa ttcacaggga cctaaaacct agtaatctag ctgtgaatga     960
agactgtgag ctgaagattc tggattttgg actggctcgg cacacagatg atgaaatgac    1020
aggctacgtg gccactaggt ggtacagggc tcctgagatc atgctgaact ggatgcatta    1080
caaccagaca gttgatattt ggtcagtggg atgcataatg gccgagctgt tgactggaag    1140
aacattgttt cctggtacag accatattaa ccagcttcag cagattatgc gtctgacagg    1200 aacaccccc gcttatctca ttaacaggat gccaagccat gaggcaagaa actatattca    1260
gtctttgact cagatgccga agatgaactt tgcaatgta tttattggtg ccaatcccct    1320
ggctgtcgac ttgctggaga agatgcttgt attggactca gataagagaa ttacagcggc    1380
```

```
ccaagcccttt gcacatgcct actttgctca gtaccacgat cctgatgatg aaccagtggc    1440
cgatccttat gatcagtcct ttgaaagcag ggacctcctt atagatgagt ggaaaagcct    1500
gacctatgat gaagtcatca gctttgtgcc accacccctt gaccaagaag agatggagtc    1560
ctgagcacct ggtttctgtt ctgttgatcc cacttcactg tgaggggaag gccttttcac    1620
gggaactctc caaatattat tcaagtgcct cttgttgcag agatttcctc catggtggaa    1680
gggggtgtgc gtgcgtgtgc gtgcgtgtta gtgtgtgtgc atgtgtgtgt ctgtctttgt    1740
gggagggtaa gacaatatga acaaactatg atcacagtga ctttacagga ggttgtggat    1800
gctccagggc agcctccacc ttgctcttct ttctgagagt tggctcaggc agacaagagc    1860
tgctgtcctt ttaggaatat gttcaatgca aagtaaaaaa atatgaattg tccccaatcc    1920
cggtcatgct tttgccactt tggcttctcc tgtgacccca ccttgacggt ggggcgtaga    1980
cttgacaaca tcccacagtg gcacggagag aaggcccata ccttctggtt gcttcagacc    2040
tgacaccgtc cctcagtgat acgtacagcc aaaaaggacc aactggcttc tgtgcactag    2100
cctgtgatta acttgcttag tatggttctc agatcttgac agtatatttg aaactgtaaa    2160 tatgttttgtg ccttaaaagg agagaagaaa gtgtagatag ttaaaagact gcagctgctg    2220
aagttctgag ccgggcaagt cgagagggct gttggacagc tgcttgtggg cccggagtaa    2280
tcaggcagcc ttcataggcg gtcatgtgtg catgtgagca catgcgtata tgtgcgtctc    2340
tctttctccc tcaccccccag gtgttgccat ttctctgctt acccttcacc tttggtgcag    2400
aggtttcttg aatatctgcc ccagtagtca gaagcaggtt cttgatgtca tgtacttcct    2460
gtgtactctt tatttctagc agagtgagga tgtgttttgc acgtcttgct atttgagcat    2520
gcacagctgc ttgtcctgct ctcttcagga ggccctggtg tcaggcaggt ttgccagtga    2580
agacttcttg ggtagtttag atcccatgtc acctcagctg atattatggc aagtgatatc    2640
acctctcttc agcccctagt gctattctgt gttgaacaca attgatactt caggtgcttt    2700
tgatgtgaaa atcatgaaaa gaggaacagg tggatgtata gcattttat tcatgccatc    2760 tgttttcaac caactatttt tgaggaatta tcatgggaaa agaccagggc ttttcccagg    2820
aatatcccaa acttcggaaa caagttattc tcttcactcc caataactaa tgctaagaaa    2880
tgctgaaaat caaagtaaaa aattaaagcc cataaggcca gaaactcctt ttgctgtctt    2940
tctctaaata tgattacttt aaaataaaaa agtaacaagg tgtctttttcc actcctatgg    3000 aaaagggtct tcttggcagc ttaacattga cttcttggtt tggggagaaa taaattttgt    3060
ttcagaattt tgtatattgt aggaatcctt tgagaatgtg attccttttg atggggagaa    3120
agggcaaatt attttaatat tttgtatttt caactttata aagataaaat atcctcaggg    3180
gtggagaagt gtcgttttca taacttgctg aatttcaggc attttgttct acatgaggac    3240
tcatatattt aagccttttg tgtaataaga agtataaag tcacttccag tgttggctgt    3300
gtgacagaat cttgtatttg ggccaaggtg tttccatttc tcaatcagtg cagtgataca    3360
tgtactccag agggacaggg tggaccccct gagtcaactg gagcaagaag gaaggaggca    3420
gactgatggc gattccctct cacccgggac tctccccctt tcaaggaaag tgaacccttta    3480 aagtaaaggc ctcatctcct ttattgcagt tcaaatcctc accatccaca gcaagatgaa    3540
ttttatcagc catgtttggt tgtaaatgct cgtgtgattt cctacagaaa tactgctctg    3600
aatattttgt aataaaggtc tttgcacatg tgaccacata cgtgttagga ggctgcatgc    3660
tctggaagcc tggactctaa gctggagctc ttggaagagc tcttcggttt ctgagcataa    3720
tgctcccatc tcctgatttc tctgaacaga aaacaaaaga gagaatgagg gaaattgcta    3780
```

```
tttttatttgt attcatgaac ttggctgtaa tcagttatgc cgtataggat gtcagacaat    3840
accactggtt aaaataaagc ctattttca aatttagtga gtttctcaag tttattatat    3900
ttttctcttg tttttattta atgcacaata tggcattata tcaatatcct ttaaactgtg    3960
acctggcata cttgtctgac agatcttaat actactccta acatttagaa aatgttgata    4020
aagcttctta gttgtacatt ttttggtgaa gagtatccag gtctttgctg tggatgggta    4080
aagcaaagag caaatgaacg aagtattaag cattggggcc tgtcttatct acactcgagt    4140
gtaagagtgg ccgaaatgac agggctcagc agactgtggc ctgagggcca aatctggccc    4200
accacctgtt tggtgtagcc tgctaagaat ggcttttaca ttttttaaatg gttgggaaag    4260 aaaaaaaaag aagtagtaga ttttgtagca tgtgatgtaa gtaatgtaaa acttaaattc    4320
cagtatccat aaataaagtt ttatgagaac aga                                 4353

<210> SEQ ID NO 3
<211> LENGTH: 2452
<212> TYPE: DNA
<213> ORGANISM: Mus musculus

<400> SEQUENCE: 3
caccccgctt tgctcagcgg tgctgggcgt ggggcgcggg ccgggtgctg cgcgcgggga      60
tccggggcgc tcgctccagc tgcttctgtg gatatgtcgg gtccgcgcgc gggattctac     120
cggcaagagc tgaacaaaac agtatgggag gtgccgcagc ggctgcaggg cctacgcccg     180
gtgggctccg cgcctacgg ctcagtctgc tcggcctacg acgcgcggct cgcgccagaag      240 gtggctgtaa agaagctgtc tcgcccttc caatcgctga tccacgcgag gaggacatac      300
cgtgagctgc gcctactcaa gcacctgaag cacgagaacg tcataggact tttggacgtc      360
ttcacgccgg ccacatccat cgaggatttc agcgaagtgt acctcgtgac gaccctgatg      420
ggcgccgacc tgaataacat cgtcaagtgt caggccctga gcgatgagca tgttcaattc      480
cttgtctacc agctgctgcg tgggctgaag tatatccact cggcgggcat catccaccgg      540
gacctgaagc ccagcaatgt agcggtgaac gaggactgcg agctgaggat cctggacttt      600
gggctagcac gccaggctga tgaggagatg accggatatg tggccacacg gtggtaccgg      660
gcgccagaga tcatgctaaa ctggatgcac tacaaccaga cagtggacat ctggtctgtg      720
ggctgcatca tggctgaact gctgcaagga aaggccctct ttcctggaaa cgactacatc      780
gaccagctga gcgaatcat ggaggtggtg ggcacgccca gtcctgaggt tctggcaaag      840
atatcctcgg agcatgcccg gacatacatc cagtctctgc ctcccatgcc ccagaaggac      900
ctcagcagtg tcttccatgg agccaacccc ctggccatag acctccttgg aagaatgctg    960
gtactagaca gcgaccagag ggtcagtgcg gccgaagcct tggcccacgc atacttcagc   1020
cagtaccatg accctgacga tgagccagag gcagagccct atgatgaaag tgttgaggcc    1080
aaggagcgca cgctggagga gtggaaggag cttacttacc aagaagtcct tagcttcaag   1140 ccctggaac cctcacagct ccctggcacc catgaaattg agcagtgagg cattgcctga    1200
agtgggagac ctgagcctgt cccctctact cagctttccg gctttcctca agaggcgcct   1260
ctcaggcagc cctgacactt aacctgggac cgacccccctt gccttgagaa actctacaca   1320
cacacacaca cacacacaca cacacacaca cacacagagg aatgcacgga tgtgtacata   1380
tgcctccctc ccattatgtg ctggagtctg ggcagtagtg tttctggacc taccttggtc    1440
cacccaggtt ctccttggga cctccgtgtg tgggatctga gtgtgtccct gtccttgtcc    1500
```

| | |
|---|---|
| aggtctcttc tgctcttgag gactatctgg attgggagga aggctaatgg gccatggtcc | 1560 |
| ctggagactc tgagggaggg ggagtcacag tggttggaga tgctcaacca ggaagtgagt | 1620 |
| ggctgaaagc agaggcaagc ccagtgtccc tcctaactga gtggcgtttc ctctggggat | 1680 |
| gggaaagctg agaccaccat cagattatct atctagtcag aaaagcctgc tgaagatttg | 1740 |
| tggttgcctg tggtatgtgg gcacatgggc atgagtatgc accctgggat acacatcaga | 1800 |
| acaaatgcag gcatgtgctg gtgtgtatga atctctgagc acccaagagg cagcagccat | 1860 |
| ttctggtctg gtgcctaagt tggagataac tcttgcctcc tctcccccca agttcctgtt | 1920 |
| ttctaatggg tcttgaatcc cagctgtgaa ctagaccaaa ggctctgaga ggtgccaaga | 1980 |
| tccattagtt taagcaaatg taagggtata ggagcagcag caggatcctg agtcacaagg | 2040 |
| gcacaatgcc agctggagag ctgatgaagt tggggtcta atctcaagga tgctaggtgg | 2100 |
| ccagcaccca cggatgtgag catggacatt cttgccccgg gaccttgatt caaagttgac | 2160 |
| aaacgtctgt ccacgttcta cctccaccaa cccttgaggt tctgcagctg gtctggggtg | 2220 |
| ctatggtttg caagtcaccc ctcatctccc catcccccag agaggagctg accaagtaac | 2280 |
| ttttgaggta gggccctgtt tgaaaacgcg ttggggggtgt aacgcctccc tgaagagaca | 2340 |
| atgatctctt gcttatcagg gaccaagggg ctctggatgt caagtgcctg caccaagagt | 2400 |
| gtgcacaata aggggcatc cctcttgctc ttgtctgtgc aaaaaaaaaa aa | 2452 |

<210> SEQ ID NO 4
<211> LENGTH: 2420
<212> TYPE: DNA
<213> ORGANISM: Homo sapiens

<400> SEQUENCE: 4

| | |
|---|---|
| tcgggcgcgg gcgcggggcg cggggctggg cccgggcgga gcggcggctg ctccggacat | 60 |
| gtcgggccct cgcgccggct tctaccggca ggagctgaac aagaccgtgt gggaggtgcc | 120 |
| gcagcggctg caggggctgc gcccggtggg ctccggcgcc tacggctccg tctgttcggc | 180 |
| ctacgacgcc cggctgcgcc agaaggtggc ggtgaagaag ctgtcgcgcc ccttccagtc | 240 |
| gctgatccac gcgcgcagaa cgtacccgga gctgcggctg ctcaagcacc tgaagcacga | 300 |
| gaacgtcatc gggcttctgg acgtcttcac gccggccacg tccatcgagg acttcagcga | 360 |
| agtgtacttg gtgaccaccc tgatgggcgc cgacctgaac aacatcgtca gtgccaggc | 420 |
| gctgagcgac gagcacgttc aattcctggt ttaccagctg ctgcgcgggc tgaagtacat | 480 |
| ccactcggcc gggatcatcc accgggacct gaagcccagc aacgtggctg tgaacgagga | 540 |
| ctgtgagctc aggatcctgg atttcgggct ggcgcgccag gcggacgagg agatgaccgg | 600 |
| ctatgtggcc acgcgctggt accgggcacc tgagatcatg ctcaactgga tgcattacaa | 660 |
| ccaaacagtg gatatctggt ccgtgggctg catcatggct gagctgctcc agggcaaggc | 720 |
| cctcttcccg ggaagcgact acattgacca gctgaagcgc atcatggaag tggtgggcac | 780 |
| acccagccct gaggttctgg caaaaatctc ctcagaacac gcccggacat atatccagtc | 840 |
| cctgccccc atgcccaga aggacctgag cagcatcttc cgtggagcca ccccctggc | 900 |
| catagacctc cttggaagga tgctggtgct ggacagtgac cagagggtca gtgcagctga | 960 |
| ggcactggcc cacgcctact tcagccagta ccacgacccc gaggatgagc cagaggccga | 1020 |
| gccatatgat gagagcgttg aggccaagga gcgcacgctg gaggagtgga aggagctcac | 1080 |
| ttaccaggaa gtcctcagct tcaagccccc agagccaccg aagccacctg gcagcctgga | 1140 |
| gattgagcag tgaggtgctg cccagcagcc cctgagagcc tgtggagggg cttgggcctg | 1200 |

```
caccottcca cagctggcct ggtttcctcg agaggcacct cccacactcc tatggtcaca    1260
gacttctggc ctaggacccc tcgccttcag gagaatctac acgcatgtat gcatgcacaa    1320
acatgtgtgt acatgtgctt gccatgtgta ggagtctggg cacaagtgtc cctgggccta    1380
ccttggtcct cctgtcctct tctggctact gcactctcca ctgggacctg actgtggggt    1440
cctagatgcc aaaggggttc ccctgcggag ttccctgtc tgtcccaggc cgacccaagg     1500
gagtgtcagc cttgggctct cttctgtccc agggctttct ggaggacgcg ctggggccgg    1560
gaccccggga gactcaaagg gagaggtctc agtggttaga gctgctcagc ctggaggtag    1620
ggggctgtct tggtcactgc tgagaccac aggtctaaga ggagaggcag agccagtgtg     1680
ccaccaggct gggcagggac aaccaccagg tgtcaaatga gaaaagctgc ctggagtctt    1740
gtgttcaccc gtgggtgtgt gtgggcacgt gtggatgagc gtgcactccc cgtgttcata    1800
tgtcagggca catgtgatgt ggtgcgtgtg aatctgtggg cgcccaaggc cagcagccat    1860
atctggcaag aagctggagc cggggtgggt gtgctgttgc cttccctctc ctcggttcct    1920
gatgccttga ggggtgtttc agactggcgg ctccagtggg ccaaagggca accacatgag    1980
catgggcagg ggctttctcc ttggatgtgg gacccacagc agcttcctga ggctgggggt    2040
gggtgggtgg gtggtttggc cttgaggacg ctagggcagg cagcacacct ggatgtggac    2100
ttggactcgg acacttctgc cctgcaccct ggcccgctct ctacctctgc ccaccgttgt    2160
ggccctgcag ccggagatct gaggtgctct ggtctgtggg tcagtcctct ttccttgtcc    2220
caggatggag ctgatccagt aacctcggag acgggaccct gcccagagct gagttggggg    2280
tgtggctctg ccctggaaag ggggtgacct cttgcctcga ggggcccagg gaagcctggg    2340
tgtcaagtgc ctgcaccagg ggtgcacaat aaaggggggtt ctctctcaaa aaaaaaaaaa    2400
aaaaaaaaaa aaaaaaaaaa                                               2420
```